United States Patent
Yamada et al.

(10) Patent No.: US 11,519,893 B2
(45) Date of Patent: Dec. 6, 2022

(54) THERAPEUTIC DRUG FOR LIPID-PEROXIDATION-INDUCED DISEASES AND SCREENING METHOD FOR THERAPEUTIC DRUGS FOR LIPID-PEROXIDATION-INDUCED DISEASES

(71) Applicants: Ken-ichi Yamada, Fukuoka (JP); FUSO PHARMACEUTICAL INDUSTRIES, LTD., Osaka (JP)

(72) Inventors: Ken-ichi Yamada, Fukuoka (JP); Saki Shinto, Fukuoka (JP); Tomomi Ide, Fukuoka (JP); Keiichi Yamamoto, Osaka (JP)

(73) Assignees: Ken-Ichi Yamada, Fukuoka (JP); FUSO PHARMACEUTICAL INDUSTRIES, LTD., Osaka (JP)

( * ) Notice: Subject to any disclaimer, the term of this patent is extended or adjusted under 35 U.S.C. 154(b) by 422 days.

(21) Appl. No.: 16/628,446

(22) PCT Filed: Jul. 5, 2018

(86) PCT No.: PCT/JP2018/025496
§ 371 (c)(1),
(2) Date: Jan. 3, 2020

(87) PCT Pub. No.: WO2019/009355
PCT Pub. Date: Jan. 10, 2019

(65) Prior Publication Data
US 2020/0158709 A1 May 21, 2020

(30) Foreign Application Priority Data
Jul. 6, 2017 (JP) .............................. JP2017-132772

(51) Int. Cl.
*G01N 33/00* (2006.01)
*G01N 33/15* (2006.01)
(Continued)

(52) U.S. Cl.
CPC ............. *G01N 33/15* (2013.01); *C01G 49/14* (2013.01); *C07C 57/00* (2013.01); *C07D 413/12* (2013.01);
(Continued)

(58) Field of Classification Search
CPC .................................................... G01N 33/15
(Continued)

(56) References Cited

U.S. PATENT DOCUMENTS

2011/0251230 A1  10/2011 Shaw et al.
2014/0038963 A1   2/2014 Hecht et al.
(Continued)

FOREIGN PATENT DOCUMENTS

JP  2008209361 A  9/2008
JP  2012506410 A  3/2012
(Continued)

OTHER PUBLICATIONS

International Search Report for International Application No. PCT/JP2018/025496; dated Oct. 9, 2018.
(Continued)

*Primary Examiner* — Christine T Mui
*Assistant Examiner* — Emily R. Berkeley
(74) *Attorney, Agent, or Firm* — Cantor Colburn LLP

(57) ABSTRACT

The present invention provides: an assay method that uses a compound represented by formula (I) as a fluorescent probe molecule and that is for detecting the lipid peroxidation suppression activity of a test compound; an assay kit that uses the assay method; a screening method that uses the assay method; and a pharmaceutical composition that is for the treatment, etc. of diseases (such as age-related macular degeneration) that are induced by lipid peroxidation reactions.

(Continued)

US 11,519,893 B2

Page 2

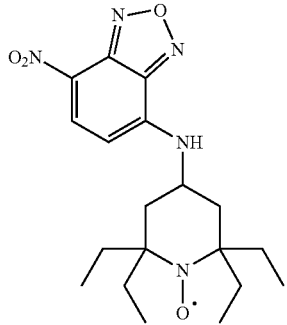

(I)

4 Claims, 18 Drawing Sheets

(51) Int. Cl.
| | |
|---|---|
| C01G 49/14 | (2006.01) |
| C07C 57/00 | (2006.01) |
| C07D 413/12 | (2006.01) |
| C12N 5/071 | (2010.01) |
| C40B 20/08 | (2006.01) |
| G01N 33/52 | (2006.01) |

(52) U.S. Cl.
CPC .............. *C12N 5/067* (2013.01); *C40B 20/08* (2013.01); *G01N 33/52* (2013.01)

(58) Field of Classification Search
USPC ........................................................ 436/92
See application file for complete search history.

(56) References Cited

U.S. PATENT DOCUMENTS

| | | |
|---|---|---|
| 2014/0242712 A1 | 8/2014 | Braslau |
| 2018/0328951 A1 | 11/2018 | Yamada et al. |

FOREIGN PATENT DOCUMENTS

| | | |
|---|---|---|
| JP | 2014510143 A | 4/2014 |
| JP | 2018189446 A | 11/2018 |
| WO | 2012138713 A2 | 10/2012 |
| WO | 2015029948 A1 | 3/2015 |

OTHER PUBLICATIONS

PCT International Preliminary Report on Patentability for International Application No. PCT/JP2018/025496 with Written Opinion of the International Searching Authority; dated Jan. 7, 2020.
Frijhoff, J et al., "Clinical Relevance of Biomarkers of Oxidative Stress"; Antioxidants & Redox Signaling, Nov. 2015, vol. 23 No. 14, pp. 1144-1170.
Ohishi, Taketoshi et al., "Development of Fluorescent probe for detecting lipid radical in-vivo and its application to disease model", Lecture abstracts of Kyushu branch conference of the Pharmaceutical Society of Japan; Nov. 25, 2012, pp. 132, vol. 29th.
Yamada, Kenichi, "Development of a Functional Contrast Agent for Targeting Lipid-derived Radicals", The Pharmaceutical Society of Japan; 2016, vol. 136, No. 8, pp. 1093-1100.
Kimura, Yuya et al., "Oxidation reaction rate of biomembrane lipid cholesterol under presence of soluble radical", Lecture abstracts (CD-ROM) of annual research presentation of the Society of Chemical Engineers, 2010, vol. 75th, p. RONBUNNO.E315, non-official translation.
Ide, Satsuki et al., "Development of Fluorescent probe for detecting lipid radical in-vivo and its application to liver cancer model", Lecture abstracts of Kyushu branch conference of the Pharmaceutical Society of Japan, Nov. 20, 2013, pp. 55, vol. 30th.
Mandavilli, B., et al. "Cell-Based Analysis of Lipid Peroxidation and Lipid Peroxidation-Derived Protein Modifications Using Fluorescence Microscopy and High Content Imaging", Free Radical Biology and Medicine, vol. 51, Dated: Nov. 1, 2011; p. S30.
Mandavilli, B., et al., "Cell-based analysis of oxidative stress, lipid peroxidation and lipid peroxidation-derived protein modifications using fluorescence microscopy", AACR Annual Meeting 2014, Dated: Apr. 5-9, 2014, pp. 512-512.
Mosmann et al., "Rapid Colorimetric Assay for Cellular Growth and Survival: Application to Proliferation and Cytotoxicity Assays", Journal of Immunological Methods, vol. 65, No. 1-2, Dated: Dec. 16, 1983, pp. 55-63.
EPO Extended European Search Report for corresponding EP Application No. 18828059.8; dated Mar. 3, 2021.
Ide, Satsuki et al., "Development of Fluorescent probe for detecting lipid radical in-vivo and its application to liver cancer model", Lecture abstracts of Kyushu branch conference of the Pharmaceutical Society of Japan, Nov. 20, 2013, vol. 30th, p. 55—With English Translation.
Kimura, Yuya et al., "Oxidation reaction rate of biomembrane lipid cholesterol under presence of soluble radical", Lecture abstracts (CD-ROM) of annual research presentation of the Society of Chemical Engineers, 2010, vol. 75th, p. RONBUNNO.E315—With English Translation.
Ohishi, Taketoshi et al., "Development of Fluorescent probe for detecting lipid radical in-vivo and its application to disease model", Lecture abstracts of Kyushu branch conference of the Pharmaceutical Society of Japan; Nov. 25, 2012, vol. 29th, p. 132—With English Translation.
Yamada, Ken-ichi, "Development of a Functional Contrast Agent for Targeting Lipid-derived Radicals", The Pharmaceutical Society of Japan; 2016, vol. 136, No. 8, pp. 1093-1100—With English Translation.
"Thiols in Oxidative Stress," University of Amsterdam, 1990, Chapter 10, pp. 93-103.
JPO Notification of Reasons for Refusal for corresponding JP Application No. 2021-051731; dated Nov. 9, 2021.
JPO Decision of Refusal for corresponding JP Application No. 2021-051731; dated Apr. 26, 2022.

FIG. 2
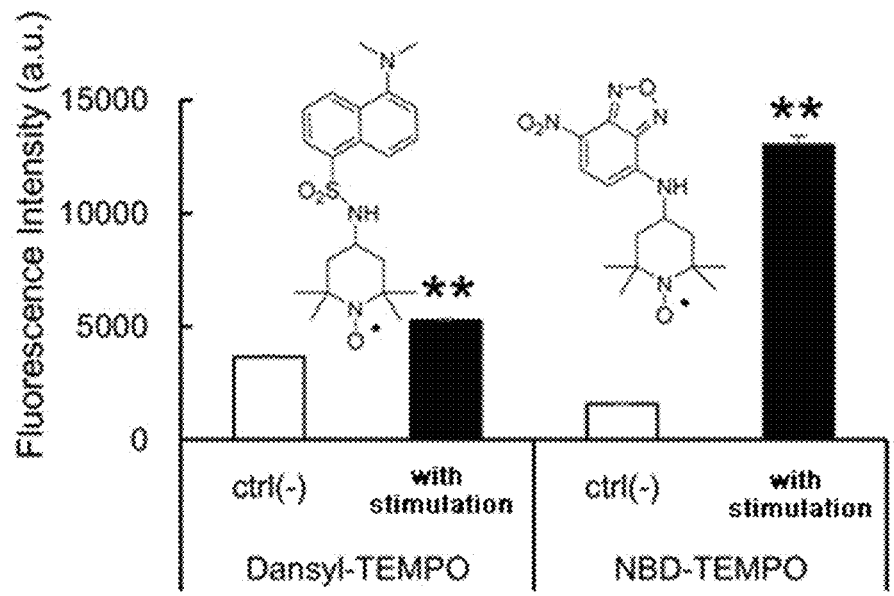
FIG. 3A
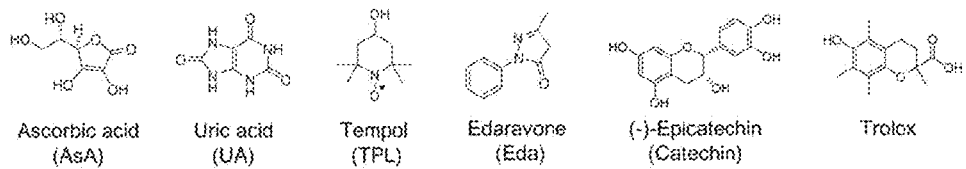
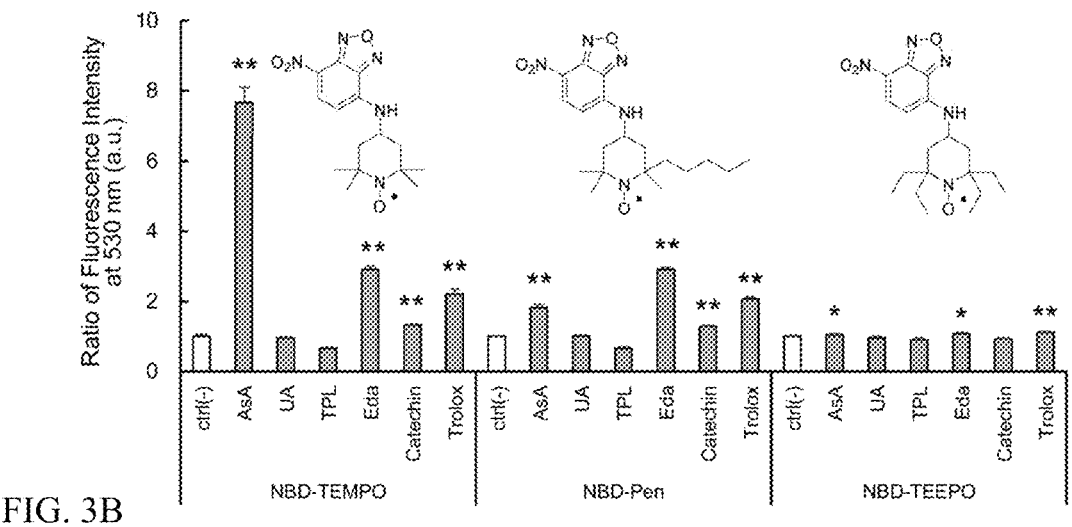
FIG. 3B

AAPH-added system

FIG. 7A
Arachidonic acid (AA)-added system
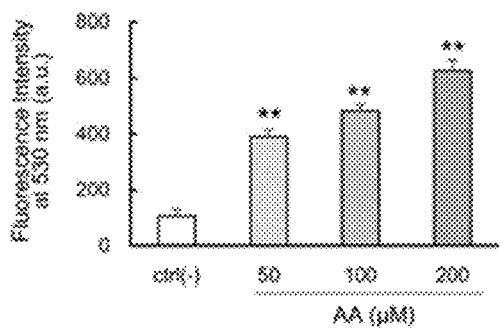
FIG. 7B
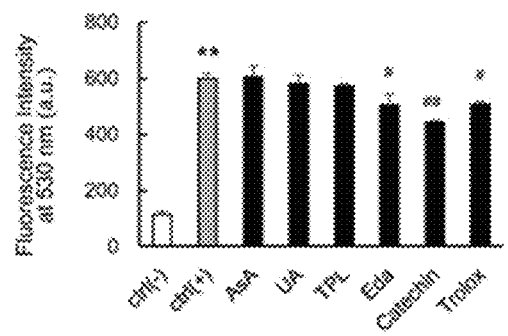
tert-butyl hydroperoxide (tBHP)-added system
FIG. 7C
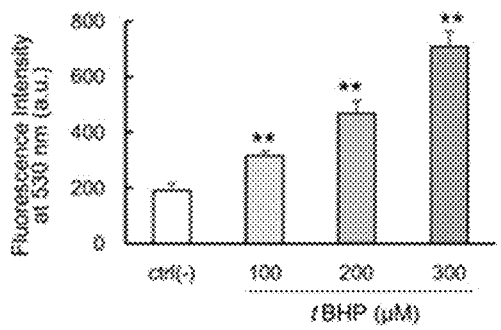
FIG. 7D
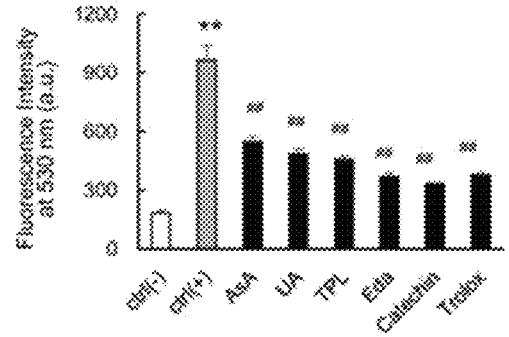
FIG. 7E
| Indicators | AA-added system | tBHP-added system | Target value |
|---|---|---|---|
| S/B ratio | 4.1 | 2.2 | 2 or more |
| CV value(%) of Background | 6.5 | 3.8 | 10% or less |
| CV value(%) of Control | 2.8 | 5.0 | 10% or less |
| Z'-factor | 0.83 | 0.62 | 0.5 or more |

FIG. 8A Arachidonic acid (AA)-added system FIG. 8B

FIG. 8C tert-butyl hydroperoxide (tBHP)-added system FIG. 8D

| Indicators | AA-added system | tBHP-added system | Target value |
|---|---|---|---|
| S/B ratio | 25.0 | 6.3 | 2 or more |
| CV value(%) of Background | 4.7 | 6.9 | 10% or less |
| CV value(%) of Control | 4.8 | 6.9 | 10% or less |
| Z'-factor | 0.86 | 0.71 | 0.5 or more |

FIG. 22

| | Main action/ action points | $LD_{50}$ (mice i.p.) | Animal administration examples |
|---|---|---|---|
| Edaravone | Antioxidative activity | (i.v.) 3.38 mmol/kg | Mice (i.p.) 57.4 μmol/kg |
| Compound V | Receptor | 0.6 mmol/kg | Mice (i.p.) 120 μmol/kg |
| Compound W | Receptor | N.D. | Mice (s.c.) 89 μmol/kg |
| Compound X | Antioxidative activity | 4.14 mmol/kg | 0.5 % in food (Estimation in mice oral 300 μ mol/kg) |
| Compound Y | Receptor | 1.92 mmol/kg | Rats (i.p.) 940 μmol/kg |
| Compound Z | Receptor | (oral) 0.6 mmol/kg | Mice (i.p.) 15 μmol/kg |

THERAPEUTIC DRUG FOR LIPID-PEROXIDATION-INDUCED DISEASES AND SCREENING METHOD FOR THERAPEUTIC DRUGS FOR LIPID-PEROXIDATION-INDUCED DISEASES

CROSS REFERENCE TO RELATED APPLICATIONS

This is the U.S. national stage of application No. PCT/JP2018/025496, filed on Jul. 5, 2018. Priority under 35 U.S.C. § 119(a) and 35 U.S.C. § 365(b) is claimed from Japanese Patent Application No. 2017-132772, filed Jul. 6, 2017; the disclosures of which are incorporated herein by reference.

TECHNICAL FIELD

The present invention provides assay methods and assay kits for exploring lipid peroxidation inhibitors, screening methods for lipid peroxidation inhibitors, and therapeutic drugs for lipid peroxidation reaction-induced diseases.

BACKGROUND ART

Diseases involving lipid radicals in lipid peroxidation reactions span a wide range of disease areas such as the cardiovascular system, the central nervous system, the respiratory system, and antibacterial drugs (Non Patent Literature 1) (see FIG. 1). However, for the diseases caused by lipid peroxidation reaction, a large number of lipid peroxides and their metabolites are involved in each disease. Thus, it is not easy to explore useful therapeutic drugs for each disease. Until now, many antioxidants have been known, but few have been approved as pharmaceuticals. Thus, it is required to provide a drug that exhibits lipid peroxidation reactions inhibitory effects.

As methods for exploring an active drug, screening methods are known. Several methods (for example, TBARs method) are known as methods for measuring lipid peroxidation reaction inhibition. However, these methods have problems such as a wide range of objects to be measured; the inability to measure samples of different absorption wavelengths when utilizing the principles of fluorescence or absorption; or the complexity of procedures such as pH manipulation or heating. Thus, there is a demand for the establishment of an assay method that specializes in the detection of lipid peroxidation reactions and that allows multi-analyte analysis under mild conditions close to those of living organisms.

The inventors of the present invention have so far developed excellent profluorescent nitroxide probe compounds capable of capturing lipid radicals (Patent Literature 1).

Age-related macular degeneration (AMD) is known to be a disease with high unmet medical needs in which treatment satisfaction is low and contribution of drugs for the treatment is low. Age-related macular degeneration is categorized based on pathogenic mechanism into two types, the atrophic (dry) and the exudative (wet). In the United States, atrophic (dry) patients accounts for a large proportion of about 85% to about 90%, while in Japan, exudative (wet) patients accounts for a large proportion of about 92%. However, effective therapeutic drugs for the atrophic (dry) disease are not known. Moreover, therapeutic drugs effective for treating and suppressing progression of age-related macular degeneration have not been developed from antioxidants.

CITATION LIST

Patent Literature

Patent Literature 1: Japanese Patent Application No. 2017-090739

Non Patent Literatures

Non Patent Literature 1: Frijhoff J et al., Antioxid. Redox Signal, 2015, 23 (14), 1144-70

SUMMARY OF INVENTION

Technical Problem

The present invention provides assay methods and assay kits for detecting lipid peroxidation inhibition, using profluorescent nitroxide probe compounds. The present invention further provides screening methods using these assay methods. The present invention also provides pharmaceutical compositions for treating lipid peroxidation reaction-induced diseases, such as age-related macular degeneration, using the active drug found by the screening methods of the present invention.

Solution to Problem

The present inventors have intensively investigated assay methods and screening methods for detecting and evaluating lipid peroxidation inhibition, and as a result, have found that assay methods using profluorescent nitroxide probe compounds and screening methods using the assay methods can readily explore candidate compounds that exhibit lipid peroxidation inhibitory activity. The present inventors have also found that these candidate compounds are useful for the treatment or prevention of diseases caused by lipid peroxidation reactions, particularly age-related macular degeneration.

That is, the present invention provides the following aspects, but is not limited thereto.
(Assay Kits and Assay Methods)
Item [1] An assay kit for detecting lipid peroxidation inhibitory activity of a test compound, comprising:
a compound represented by formula (I):

[Formula 1]

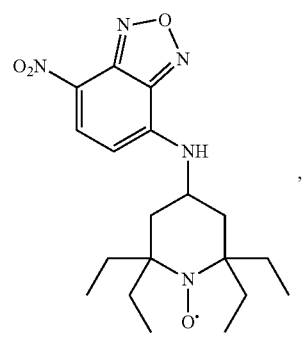

a liposome, and
at least one compound selected from the group consisting of 2,2'-azobis(2-aminopropane) dihydrochloride and a divalent iron ion source material
in a buffer.

Item [1-2] The assay kit according to item [1], wherein the compound represented by the formula (I) has a concentration of 1.0 to 20.0 μM,
the liposome is prepared from egg yolk-derived phosphatidylcholine and dihexadecyl hydrogen phosphate, the egg yolk-derived phosphatidylcholine has a concentration of 5.0 to 10.0 mg/mL, the dihexadecyl hydrogen phosphate has a concentration of 0.01 to 1.0 mg/mL, the test compound has a concentration of 5 to 100 μM,
the 2,2'-azobis(2-aminopropane) dihydrochloride has a concentration of 5 to 50 mM, and the divalent iron ion source has a concentration of 0.5 to 5 mM.

Item [2] The assay kit according to item [1], wherein the divalent iron ion source material is iron(II) sulfate.

Item [3] The assay kit according to [1] or [2], comprising a package insert showing an activity value of a compound having lipid peroxidation inhibitory activity.

Item [4] An assay kit for detecting lipid peroxidation inhibitory activity of a test compound, comprising:
a compound represented by formula (I):

[Formula 2]

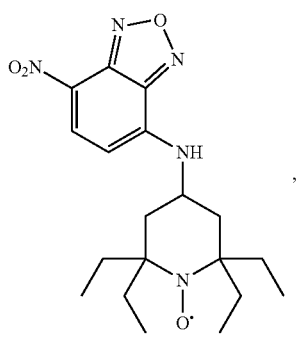

(I)

a cultured cell, and
at least one compound selected from the group consisting of arachidonic acid and tert-butyl hydroperoxide
in a buffer.

Item [4-2] The assay kit according to item [4], wherein the compound represented by the formula (I) has a concentration of 1.0 to 20.0 μM;
the cultured cell has a concentration of $1\times10^4$ to $1\times10^5$ cells,
the test compound has a concentration of 5 to 500 μM,
the arachidonic acid has a concentration of 100 to 400 μM, and
the tert-butyl hydroperoxide has a concentration of 100 to 400 μM.

Item [5] The assay kit according to item [4], wherein the cultured cell is a human hepatoma-derived HepG2 cell.

Item [6] The assay kit according to item [4] or [5], comprising a package insert showing an activity value of a compound having lipid peroxidation inhibitory activity.

Item [7] An assay kit comprising any two or more of assay kits according to items [1] to [6].

Item [7-2] The assay kit according to item [7], comprising a combination of:
an assay kit wherein a reaction initiator is 2,2'-azobis(2-aminopropane) dihydrochloride; and
an assay kit wherein a reaction initiator is iron(II) sulfate.

Item [7-3] The assay kit according to item [7], comprising a combination of:
an assay kit wherein a reaction initiator is arachidonic acid, and
an assay kit wherein a reaction initiator is tert-butyl hydroperoxide.

Item [8] An assay method for measuring lipid peroxidation inhibitory activity, comprising:
i) preparing a buffer containing a compound represented by formula (I) and a liposome;
ii) adding at least one compound selected from the group consisting of 2,2'-azobis(2-aminopropane) dihydrochloride and a divalent iron ion source material;
iii) adding a test compound;
iv) measuring fluorescence; and
v) determining an activity value of the test compound from the result of measuring the fluorescence.

Item [9] An assay method for measuring lipid peroxidation inhibitory activity, comprising:
i) preparing a buffer containing a compound represented by formula (I) and a cultured cell;
ii) adding at least one compound selected from the group consisting of arachidonic acid and tert-butyl hydroperoxide,
iii) adding a test compound;
iv) measuring fluorescence; and
v) determining an activity value of the test compound from the result of measuring the fluorescence.

Item [10] The assay method according to item [8] or [9], comprising
vi) comparing with an activity value of a compound serving as an indicator of lipid peroxidation inhibitory activity.

Item [11] The assay method according to any one of items [8] to [10], for use with a microwell plate.

Item [11-2] The assay method according to item [11], comprising:
i) dispensing a solution of a test compound into the microwell plate;
ii) dispensing a solution containing a compound represented by formula (I) and a liposome or a cultured cell into each well;
iii) when using the liposome, dispensing a solution containing at least one compound selected from the group consisting of 2,2'-azobis(2-aminopropane) dihydrochloride and a divalent iron ion source material into the each well, and
when using the cultured cell, dispensing a solution containing at least one compound selected from the group consisting of arachidonic acid and tert-butyl hydroperoxide into the each well; and
iv) measuring fluorescence with a microplate reader.

(Screening Method)

Item [12] A screening method for selecting a candidate compound having high lipid peroxidation inhibitory activity, comprising:
i) selecting a test compound from a compound library;
ii) performing a screening using the test compound by the assay method according to item [8] using 2,2'-azobis(2-aminopropane) dihydrochloride, and selecting a compound having a high activity value; and
iii) then, performing a screening using the compound having a high activity value in ii) by the assay method according to item [8] using a divalent iron ion source material, and selecting a compound having a high activity value.

Item [13] The screening method according to item [12], when the compound library is a library containing an unapproved compound as a food or pharmaceutical, further comprising, in addition to the screening method according to item [12]:
i) performing a screening by the assay method according to item [9] using arachidonic acid, and selecting a compound having a high activity value;
ii) performing a screening by the assay method according to item [9] using tert-butyl hydroperoxide, and selecting a compound having a high activity value; and
iii) selecting a compound having high activity values in both of the screenings of i) and ii).

Item [14] The screening method according to item [12] or [13], when the compound library is a library containing an unapproved compound as a food or pharmaceutical, further comprising, in addition to the screening method according to item [12]:
i) performing a screening by an assay method according to an MTT method using a culture medium containing a cultured cell, a test compound and arachidonic acid, and selecting a compound having high cell viability;
ii) performing a screening by an assay method according to an MTT method using a culture medium containing a cultured cell, a test compound, and tert-butyl hydroperoxide, and selecting a compound having high cell viability; and
iii) selecting a compound having high cell viability in both of the screenings of i) and ii).

Item [15] The screening method according to item [13] or [14], comprising:
i) selecting a structural analog of a compound selected by the screening method according to item [13] or [14] from a compound library;
ii) performing the screening method according to item [13] for the compound selected in i) and optionally the compound selected by the screening method according to item [13] or [14], and selecting a compound having a high activity value;
iii) performing the screening method according to item [14] for the compound selected in i) and optionally the compound selected by the screening method according to item [13] or [14], and selecting a compound having high cell viability;
iv) selecting a candidate compound having a high activity value and high cell viability in both of the screening methods of ii) and iii);
v) performing an assay method using a culture medium containing a cultured cell for the compound selected in i) and optionally the compound selected by the screening method according to item [13] or [14], and selecting a candidate compound having high cell viability, and
vi) selecting a candidate compound from the compound selected in iv) and the compound selected in v).

Item [16] The screening method according to any one of items [12] to [15], wherein the compound library is Core Library of Drug Discovery Initiative, the University of Tokyo, or Prestwick Chemical Library.

Item [16-2] The screening method according to any one of items [12] to [15], wherein the screening method is a high throughput screening method.

(Medical Use)

Item [17] A pharmaceutical composition for preventing or treating a lipid peroxidation reaction-induced disease or inhibiting progression of the lipid peroxidation reaction-induced disease in a subject, comprising an effective amount of at least one compound selected from the group consisting of a group:
apomorphine ((R)-(−)-apomorphine hydrochloride), eseroline ((−)-eseroline fumarate), ethoxyquine (6-ethoxy-2,2,4-trimethyl-1,2-dihydroquinoline), methyldopa (methyldopa sesquihydrate), olanzapine (2-methyl-4-(4-methyl-1-piperazinyl)-10H-thieno[2,3-b][1,5]benzodiazepine, methyl 3-amino-4-(phenylamino)benzoate (compound 52), methyl 3-amino-4-((4-methoxyphenyl)amino)benzoate (compound 52-1), methyl 3-amino-4-((3-methoxyphenyl)amino)benzoate (compound 52-3), methyl 3-amino-4-(benzylamino)benzoate (compound 52-4), methyl 3-amino-4-((1-phenylethyl)amino)benzoate (compound 52-5), 1-(4-(trifluoromethoxy)phenyl)indolin-5-amine (compound 78), 1-(3,5-dimethylphenyl)-1H-indol-6-amine (compound 78-3), 1-(3,5-dimethylphenyl)indolin-6-amine (compound 78-4), 1-(4-methoxyphenyl)-1H-indol-6-amine (compound 78-5), 1-(4-(methylthio)phenyl)-1H-indol-6-amine (compound 78-6), 1-(4-(trifluoromethoxy)phenyl)-1H-indol-5-amine (compound 78-8).

Item [18] The pharmaceutical composition according to item [17], wherein the disease is selected from the group consisting of Alzheimer-type dementia, chronic kidney diseases, diabetic neuropathy, liver disorder, age-related macular degeneration, postischemic brain disorder, vascular dementia, arteriosclerosis, Parkinson's disease, multiple sclerosis, cancer, asthma, hypertension, cardiovascular diseases, and age-related eye disease.

Item [19] The pharmaceutical composition according to item [17], wherein the disease is age-related macular degenerative disease.

Item [20] A method for preventing or treating a lipid peroxidation reaction-induced disease or inhibiting progression of the lipid peroxidation reaction-induced disease, with at least one compound selected from the group consisting of the group described in item [17].

Item [21] Use of at least one compound selected from the group consisting of the group described in item [17] in the manufacture of a medicament for preventing or treating a lipid peroxidation reaction-induced disease or inhibiting progression of the lipid peroxidation reaction-induced disease.

Item [22] Use of at least one compound selected from the group consisting of the group described in item [17], for preventing or treating a lipid peroxidation reaction-induced disease or inhibiting progression of the lipid peroxidation reaction-induced disease.

Effects of Invention

The assay kit of the present invention and the screening method using the assay kit enable to easily explore a compound having a lipid peroxidation inhibitory effect. Furthermore, the compounds found by the screening method of the present invention are useful for treatment of lipid peroxidation reaction-induced diseases (for example, age-related macular degeneration), or the like.

BRIEF DESCRIPTION OF DRAWINGS

FIG. 2 is a chart showing the result of a test for evaluating the responsiveness of profluorescent nitroxide probes to lipid peroxidation reaction. Liposomes (2.5 mg/mL EggPC, 0.1 mg DCP), 5.0 μM profluorescent nitroxide, and 20 mM AAPH were mixed, and after 40 minutes, the fluorescence intensity (NBD-TEMPO: $\lambda_{Ex}/\lambda_{Em}$=470/530 nm, Dansyl-TEMPO: $\lambda_{Ex}/\lambda_{Em}$=300/500 nm) was measured (n=3, mean+S.D., **p<0.01 v.s. ctrl(−)).

FIG. 3A-FIG. 3B is a chart showing the result of a test for evaluating the reactivity between profluorescent nitroxide probes and various reductants. Liposomes (2.5 mg/mL EggPC, 0.1 mg DCP), 5.0 μM profluorescent nitroxide, and 50 μM antioxidant were mixed, and after 40 minutes, the fluorescence intensity ($\lambda_{Ex}/\lambda_{Em}$=470/530 nm) was measured. The ratio of the fluorescence intensity is a value obtained by dividing the fluorescence intensity of the probe after reaction with the various antioxidants by the fluorescence intensity of ctrl(−). FIG. 3A Chemical structure of the antioxidant used in this study; FIG. 3B Ratio of fluorescence intensity due to the reaction between the probe and the antioxidant (n=3, mean+S.D., *p<0.05, **p<0.01 v.s. ctrl (−)).

FIG. 5A Stimulation concentration-dependency (AAPH 0-20 mM); FIG. 5B Antioxidant concentration-dependency (AAPH 20 mM, AsA 0-20 μM) of NBD-TEEPO fluorescence responsiveness. Comparison of FIG. 5C lipid peroxidation reaction evaluation method using NBD-TEEPO (AAPH 20 mM, antioxidant 10 μM) and FIG. 5D TBARS assay (AAPH 20 mM, antioxidant 10 μM) (n=3, mean+S.D., **p<0.01 v.s. ctrl(−), *p<0.05, **p<0.01 v.s. ctrl(+)).

FIG. 6A Stimulation concentration-dependency ($FeSO_4$ 0-2 mM); FIG. 6B Antioxidant concentration-dependency ($FeSO_4$ 1 mM, Eda 0-20 μM) of NBD-TEEPO fluorescence responsiveness. Comparison of FIG. 6C lipid peroxidation reaction evaluation method using NBD-TEEPO ($FeSO_4$ 1 mM, antioxidant 10 μM) and FIG. 6D TBARS assay ($FeSO_4$ 1 mM, antioxidant 10 μM) (n=3, mean+S.D., **p<0.01 v.s. ctrl(−), ##p<0.05, ##p<0.01 v.s. ctrl(+)).

FIG. 7A-FIG. 7E is charts showing the results of a test for evaluating intracellular lipid peroxidation reaction in cultured cell systems. To 1.0×10$^4$ HepG2 cells, 5.0 μM NBD-TEEPO and 50 μM various oxidants and antioxidants were added, and changes of the fluorescence intensity ($\lambda_{Ex}/\lambda_{Em}$=470/530 nm) were measured. FIG. 7A Fluorescence intensity of NBD-TEEPO at 45 minutes after addition of AA (0 to 200 μM); FIG. 7B Fluorescence intensity of NBD-TEEPO at 45 minutes after addition of 200 μM AA and 50 μM antioxidant; FIG. 7C Fluorescence intensity of NBD-TEEPO at 45 minutes after addition of tBHP (0 to 300 μM); FIG. 7D Fluorescence intensity of NBD-TEEPO at 45 minutes after addition of 300 μM tBHP and 50 antioxidant; FIG. 7E S/B ratios, CV values, and Z'-factors (AA-added system: 45 minutes after addition of 200 μM AA; tBHP-added system: 45 minutes after addition of 300 μM tBHP) (n=3, mean+S.D., **p<0.01 v.s. ctrl(−), #p<0.05, ##p<0.01 v.s. ctrl(+)).

FIGS. 8A-FIG. 8E is charts showing the results of a test for evaluating changes in lipid peroxidation-induced cell viability in cultured cell systems using an MTT assay. To 1.0×10$^4$ HepG2 cells were added 50 μM various oxidants and antioxidants, and the cell viability after 24 hours was measured by an MTT assay ($\lambda_{max}$=570 nm). The cell viability was calculated with a 0 μM oxidation stimulus and 0 μM antioxidant as 100%. FIG. 8A Cell viability at 24 hours after addition of AA (0 to 100 μM); FIG. 8B Cell viability at 24 hours after addition of 100 μM AA and 50 μM antioxidant; FIG. 8C Cell viability at 24 hours after addition of tBHP (0 to 100 μM); FIG. 8D Cell viability at 24 hours after addition of 100 μM tBHP and 50 μM antioxidant; (e) S/B ratios, CV values, and Z'-factors (AA-added system: 24 hours after addition of 100 μM AA, tBHP-added system: 24 hours after addition of 100 μM tBHP). (n=3, mean+S.D., **p<0.01 v.s. ctrl(−), #p<0.05, ##p<0.01 v.s. ctrl(+)).

FIG. 13A Activity value of each compound at 45 minutes after addition of AA; FIG. 13B Activity value of each compound at 60 minutes after addition of tBHP; FIG. 13C Plot of activity values in the AA-added system and tBHP-added system; FIG. 13D) Enlarged view of the part in which the activity value in the AA-added system is 30% or more and the activity value in the tBHP-added system is 50% or more in FIG. 13C.

FIG. 14A Activity value of each compound at 24 hours after addition of AA; FIG. 14B Activity value of each compound at 24 hours after addition of tBHP; FIG. 14C Plot of activity values in the AA-added system and tBHP-added system; FIG. 14D Enlarged view of the part in which the activity value in the AA-added system is 30% or more and the activity value in the tBHP-added system is 50% or more in FIG. 14C.

FIG. 15A Activity value of each compound at 45 minutes after addition of AA; FIG. 15B Activity value of each compound at 60 minutes after addition of tBHP; FIG. 15C Plot of activity values in the AA-added system and tBHP-added system; FIG. 15d Enlarged view of the part in which the activity values in the AA-added system and the activity value in the tBHP-added system are 50% or more in FIG. 15C.

FIG. 16A Activity value of each compound at 24 hours after addition of AA; FIG. 16B Activity value of each compound at 24 hours after addition of tBHP; FIG. 16C Plot of activity values in the AA-added system and tBHP-added system; FIG. 16D Enlarged view of the part in which the activity value in the AA-added system is 0% or more and the activity value in the tBHP-added system is 40% or more in FIG. 16C.

FIG. 18A Activity value of each compound at 40 minutes after starting measurement in an AAPH system; FIG. 18B Activity value of each compound at 180 minutes after starting measurement in an $Fe^{2+}$ system.

FIG. 19A Plot of activity values of the AAPH system and the $Fe^{2+}$-added system at primary screening; FIG. 19B Target disease areas of the top 16 compounds; FIG. 19C Enlarged view of the part in which the activity value in the AAPH system is 0.7 or ore and the activity value in the $Fe^{2+}$-added system is 0.8 or more in FIG. 19A.

FIG. 20A AMD model mouse production schedule; FIG. 20B ONL measurement method in which ONL thickness was measured over 27 points (A-center-Z) every 180 μm (left: observation field of 4 times, right: observation field of 60 times).

FIG. 21A ONL bright field image (observation magnification: 60 times); FIG. 21B ONL thickness (model compound: compound W). The left represents the inferior hemisphere of eyeball, and the right represents the superior hemisphere of eyeball. FIG. 21C Mean thickness of the ONL at points Q to T (n=3-5, mean+S.D., *p<0.05, **p<0.01 v.s. ctrl(−), #p<0.05, ##p<0.01 v. s. ctrl(+)).

FIG. 22 is a table summarizing main action/action points, half-lethal dose ($LD_{50}$) and animal administration examples for the activity indicator compound and candidate compounds. The main action/action points, $LD_{50}$ and animal administration examples were shown for Edaravone and the five compounds used in this study. Here, oral represents oral administration, s.c. represents subcutaneous injection, and i.v. represents intravenous injection.

Figure 1:
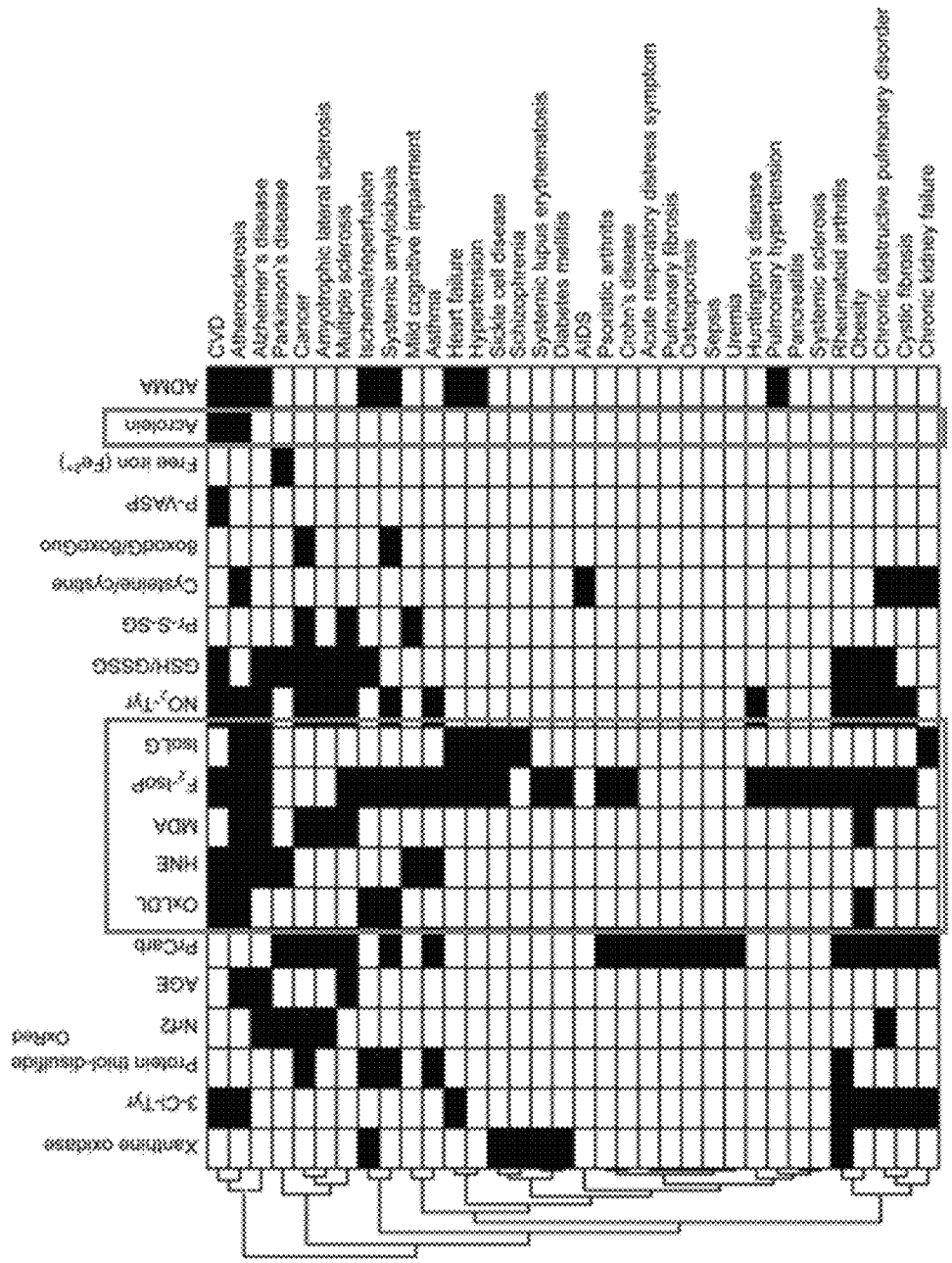
FIG. 1 is a chart showing the relationship between lipid peroxidation reaction and diseases.

DESCRIPTION OF EMBODIMENTS (Assay Method and Assay Kit)

The present inventors provide assay methods and assay kits for developing screening methods (for example, high-throughput screening methods) capable of testing and evaluating a large number of compounds at once for the purpose of exploring lipid peroxidation inhibitors.

The present invention provides an assay kit for detecting lipid peroxidation inhibitory activity of a test compound, comprising
a compound represented by formula (I):

[Formula 3]

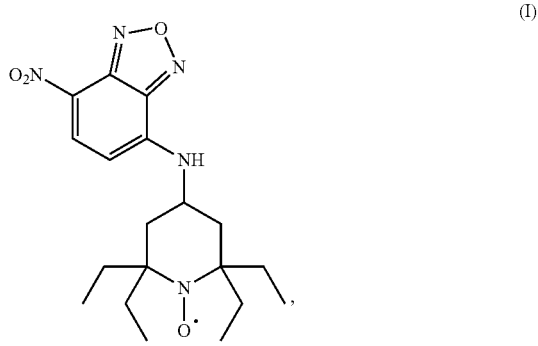

(I)

a liposome, and
at least one compound selected from the group consisting of 2,2'-azobis(2-aminopropane) dihydrochloride and a divalent iron ion source material
in a buffer.

Examples of the liposome used in the assay kit of the present invention include a liposome produced from egg yolk-derived phosphatidylcholine (egg yolk-derived phosphatidylcholine (Egg PC)) and dihexadecyl hydrogen phosphate (DCP) as a lipid source.

Examples of the radical reaction initiator include at least one compound selected from the group consisting of either 2,2'-azobis(2-aminopropane) dihydrochloride (hereinafter referred to as "AAPH") or divalent iron ion source materials (for example, $FeSO_4$).

The assay kit of the present invention includes a solution of buffer (for example, phosphate buffer).

Profluorescent Nitroxide Compound

In the assay method and the assay kit of the present invention, a profluorescent nitroxide compound represented by formula (I) is used as a lipid radical scavenger. The profluorescent nitroxide compound is described in the literature by the present inventors (for example, Japanese Patent Application No. 2017-090739).

Here, nitroxide (NO.) refers to a stable radical having paramagnetism. The nitroxide has a property of attenuating fluorescence due to photo-induced electron transfer accompanied by a charge separation state and intersystem crossing by electron-spin exchange. Profluorescent nitroxide in which a fluorescent chromophore is covalently bonded to nitroxide is in an intramolecular quenching state. However, it has been confirmed that when nitroxide reacts with free radicals and loses the paramagnetism, it is in a fluorescent emission state. Namely, the profluorescent nitroxide is useful as a probe for detecting lipid radical scavenging by fluorescence observation, and enables to evaluate the lipid radical scavenging by measuring fluorescence intensity.

Most of the lipid molecules to be detected are present in biological membranes and form a hydrophobic environment. Thus, an environmentally responsive fluorescent chromophore that emits selectively high fluorescence in hydrophobic environments while the fluorescence is attenuated in hydrophilic environments is optimal. Examples of the fluorescent chromophore include fluorescent chromophores widely used in the lipid field such as biological membrane phase transition and membrane fusion or intracellular lipid metabolism, for example, nitrobenzofurazan (hereinafter referred to as "NBD")) and 5-(dimethylamino)naphthalene-1-sulfonyl chloride) (hereinafter referred to as "Dansyl").

Examples of a probe molecule that is an α-position substituent of the fluorescent nitroxide compound include 2,2,6,6-tetramethylpiperidin-1-oxyl (hereinafter referred to as "TEMPO"), 2,2,6,6-tetraethylpiperidin-1-oxyl (hereinafter referred to as "TEEPO"), and 2,2,6-trimethyl-6-pentyl-piperidin-1-oxyl (hereinafter referred to as "Pen").

For selecting a profluorescent nitroxide compound suitable for the assay methods and assay kits of the present invention, each of the fluorophore molecule and probe molecule are optimized. The optimization of the fluorophore molecule is performed by testing the responsiveness to lipid peroxidation reaction.

The optimization of the probe molecule that is an α-position substituent of the fluorescent nitroxide compound is performed by a test for evaluating the reactivity with reductants and a test for evaluating the reactivity with oxidants. In the assay method of the present invention, inhibition is evaluated by inhibition of lipid peroxidation reaction by a reductant (i.e., an antioxidant), that is, whether or not an increase in the fluorescence intensity due to the lipid peroxidation reaction once occurred can be reduced by the antioxidant (for example, a test compound). In this case, a direct reaction of the probe molecule with the antioxidant to cause an increase of fluorescence intensity leads to detection of false negatives. Thus, first, the reactivity of the probe molecule with antioxidants is examined.

Then, the responsiveness of the probe molecule to the lipid peroxidation reaction is examined by a test for evaluating the reactivity of the probe molecule on a profluorescent nitroxide compound with oxidants. Here, reactive oxygen species •OH is generated by hydrogen peroxide and $Fe^{2+}$. Lipid peroxidation reaction is caused by liposomes and AAPH.

From the results of the test, the NBD-TEEPO compound that exhibits the highest reduction resistance and high responsiveness to the lipid peroxidation reaction is selected as the profluorescent nitroxide compound.

Establishment of Assay Method and Assay Kit

The present invention provides an assay method and an assay kit using the NBD-TEEPO compound represented by the formula (I). The assay method and the assay kit can be applied to a screening method.

Cell-Free Based Assay Methods

The present invention provides a cell-free based assay method for detecting lipid peroxidation inhibitory activity, using an NBD-TEEPO compound represented by formula (I).

Similar to the above method for optimization of profluorescent nitroxide compounds, liposomes are used as lipid, and AAPH and $FeSO_4$ are used as radical reaction initiators. In both AAPH and $Fe^{2+}$ systems, the fluorescence intensity of the probe increases concentration-dependently. In the AAPH system, when a water-soluble antioxidant (for example, ascorbic acid (AsA)) is used, the increase in fluorescence is inhibited concentration-dependently, while in the $Fe^{2+}$ system, when a lipophilic antioxidant (for example, Edaravone (eda)) is used, the increase in fluorescence is inhibited concentration-dependently. In both assay methods, by using a plurality of known antioxidants, it can be found that the assay method of the present invention is an assay method that can evaluate the lipid peroxidation reaction and the lipid peroxidation reaction inhibitory effect of antioxidants.

Further, when comparing the result of the assay method of the present invention with the result of 2-thiobarbituric acid reactive substance (hereinafter referred to as "TBARS") method, which is known as a method to measure the lipid peroxidation inhibitory effect, using the same known antioxidants, similar results are obtained. It can be found that the assay method of the present invention is an assay method that can evaluate the lipid peroxidation reaction and the inhibitory effect of antioxidants to the reaction. Moreover, the assay method of the present invention does not require a complicated procedure which is required in the TBARS method.

In one embodiment, a specific assay method includes the following steps:
i) preparing a buffer containing a compound represented by formula (I) and liposomes;
ii) adding at least one compound selected from the group consisting of 2,2'-azobis(2-aminopropane) dihydrochloride and a divalent iron ion source material;
iii) adding a test compound;
iv) measuring fluorescence; and
v) determining an activity value of the test compound from the result of measuring the fluorescence.

In one embodiment, the cell-free based assay kit of the present invention includes a combination of:
an assay kit in which the reaction initiator is 2,2'-azobis(2-aminopropane) dihydrochloride; and
an assay kit in which the reaction initiator is iron(II) sulfate.

Composition of Cell-Free Based Assay Kit

In the cell-free based assay kit of the present invention, the compound represented by the formula (I) has a concentration of 1.0 to 20.0 μM (for example, 5.0 to 20.0 μM, typically 5.0 μM);

the liposome is prepared from egg yolk-derived phosphatidylcholine and dihexadecyl hydrogen phosphate, and the egg yolk-derived phosphatidylcholine has a concentration of 5.0 to 10.0 mg/mL (for example, 2.5 mg/mL) and the dihexadecyl hydrogen phosphate has a concentration of 0.01 to 1.0 mg/mL (for example, 0.1 mg/mL), the test compound has a concentration of 5 to 100 µM (for example, 10 µM);

the 2,2'-azobis(2-aminopropane) dihydrochloride has a concentration of 5 to 50 mM (for example, 20 mM), and a divalent iron ion source material (for example, $FeSO_4$) has a concentration of 0.5 to 50 mM (for example, 1 mM).

Furthermore, since the cell-free based assay method of the present invention has sufficient values in the indicators representing the quality of screening system (for example, S/B ratio, CV value, Z'-factor), it can be applied to a screening method.

Cell-Based Assay Method

The present invention provides, in addition to the cell-free based assay method described above, a cell-based assay method for detecting lipid peroxidation inhibitory activity using an NBD-TEEPO compound represented by formula (I).

The cell-based assay method is performed using cultured cells (for example, human hepatoma-derived HepG2 cells) instead of liposomes used in the cell-free based assay, and using arachidonic acid (hereinafter referred to as "AA") and tert-butyl hydroperoxide (hereinafter referred to as "tBHP") instead of AAPH and a divalent iron ion source material as radical reaction initiators.

In one embodiment, a specific assay method includes the following steps:

i) preparing a buffer containing a compound represented by formula (I) and a cultured cell;
ii) adding at least one compound selected from the group consisting of arachidonic acid and tert-butyl hydroperoxide,
iii) adding a test compound;
iv) measuring fluorescence; and
v) determining an activity value of the test compound from the result of measuring the fluorescence.

In one embodiment, the cell-based assay kit of the present invention includes a combination of:

an assay kit in which a reaction initiator is arachidonic acid; and an assay kit in which a reaction initiator is tert-butyl hydroperoxide.

Composition of Cell-Based Assay Kit

In the cell-based assay kit of the present invention, the compound represented by formula (I) has a concentration of 1.0 to 20.0 µM (for example, 5.0 µM), the cultured cell has a concentration of $1 \times 10^4$ to $1 \times 10^5$ cells (for example, $1 \times 10^4$ cells), the test compound has a concentration of 5 to 500 µM (for example, 50 µM);

the arachidonic acid has a concentration of 100 to 400 µM (for example, 200 µM), and the tert-butyl hydroperoxide has a concentration of 100 to 400 µM (for example, 300 µM).

Furthermore, since the cell-based assay method of the present invention has sufficient values in the indicators representing the quality of screening system (for example, S/B ratio, CV value, Z'-factor), it can be applied to a screening method.

The assay kit of the present invention may include a package insert showing an activity value of a compound having lipid peroxidation inhibitory activity. Evaluation of lipid peroxidation inhibitory activity of a test compound can be performed by comparing the activity value of lipid peroxidation inhibition of the test compound obtained using the assay kit or assay method of the present invention with the activity value of the indicator compound shown in the package insert.

In one embodiment, the assay method of the present invention includes a combination of at least two or more assay methods selected from the group consisting of:

a cell-free based assay method in which the reaction initiator is 2,2'-azobis(2-aminopropane) dihydrochloride;

a cell-free based assay method in which the reaction initiator is iron(II) sulfate;

a cell-based assay method in which the reaction initiator is arachidonic acid; and a cell-based assay method in which the reaction initiator is tert-butyl hydroperoxide.

In one embodiment, the assay kit of the present invention includes a combination of at least two or more assay kits selected from the group consisting of:

a cell-free based assay kit in which the reaction initiator is 2,2'-azobis(2-aminopropane) dihydrochloride;

a cell-free based assay kit in which the reaction initiator is iron(II) sulfate;

a cell-based assay kit in which the reaction initiator is arachidonic acid; and a cell-based assay kit in which the reaction initiator is tert-butyl hydroperoxide.

Lipid peroxidation-induced cell death is caused in the process in which lipid peroxidation reaction promotes development and progression of diseases (Reference: Uchida K., Prog. Lipid Res., 2003, 42(4), 318-43). A method using 3-(4,5-dimethyl-2-thiazolyl)-2,5-diphenyltetrazolium bromide (hereinafter referred to as "MTT") is used for evaluation of cell viability. It is also known that the MTT method can be carried out by plate assay.

In one embodiment, the assay method of the present invention includes an assay method according to an MTT method, including the following steps:

i) performing an assay method according to an MTT method using a culture medium containing a cultured cell, a test compound and arachidonic acid, and selecting a compound having high cell viability; and/or ii) performing an assay method according to an MTT method using a culture medium containing a cultured cell, a test compound and tert-butyl hydroperoxide, and selecting a compound having high cell viability.

The assay method and the assay kit of the present invention may include the assay method and kit according to an MTT method in combination with the cell-free based and/or cell-based assay method and the assay kit of the present invention.

Since this MTT method has sufficient values in the indicators representing the quality of screening system (for example, S/B ratio, CV value, Z'-factor), it can be applied to a screening method.

Any assay method of the present invention can also be performed with a microwell plate. Examples of the microwell plate include a porous plate (for example, a 96-well plate and a 384-well plate), but are not limited to these. For example, commercially available microwell plates can also be used.

In one embodiment, a measurement by the assay method of the present invention using a microwell plate includes the following steps:

i) dispensing a solution of a test compound into the microwell plate;

ii) dispensing a solution containing a compound represented by formula (I) and a liposome or a cultured cell into each well;
iii) when using the liposome, dispensing a solution containing at least one compound selected from the group consisting of 2,2'-azobis(2-aminopropane) dihydrochloride and a divalent iron ion source material into the each well, and when using the cultured cell, dispensing a solution containing at least one compound selected from the group consisting of arachidonic acid and tert-butyl hydroperoxide into the each well; and
iv) measuring fluorescence with a microplate reader.

(Screening Method)

The present invention provides a screening method including a screening step using the assay method of the present invention for a compound library to explore compounds having lipid peroxidation inhibitory activity.

Figure 9A:
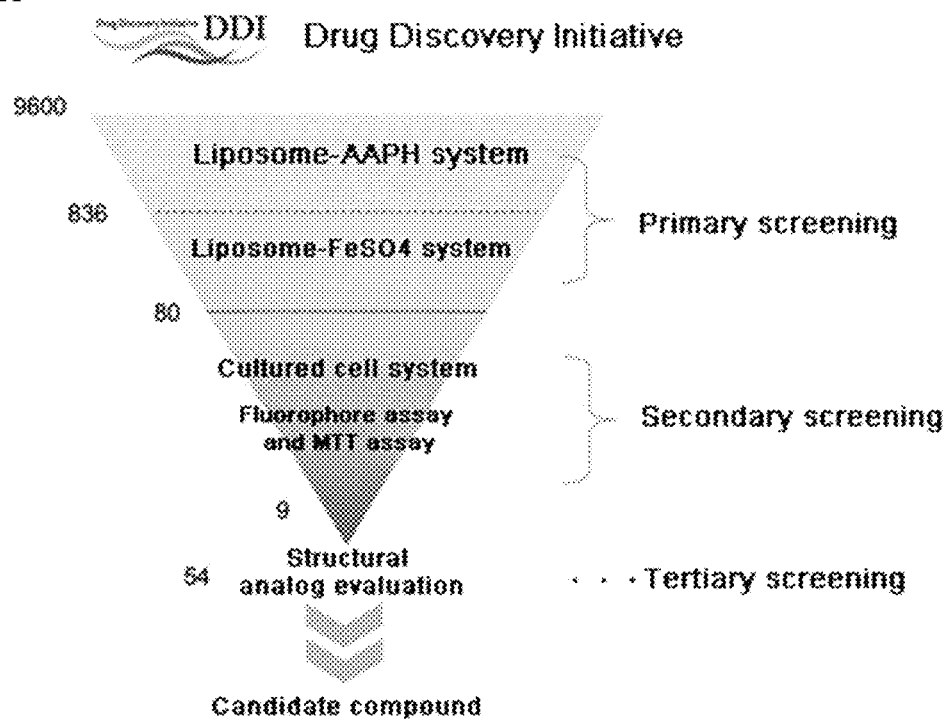
FIGS. 9A-FIG. 9B is drawings showing schematic diagrams of screening methods.
Figure 9B:
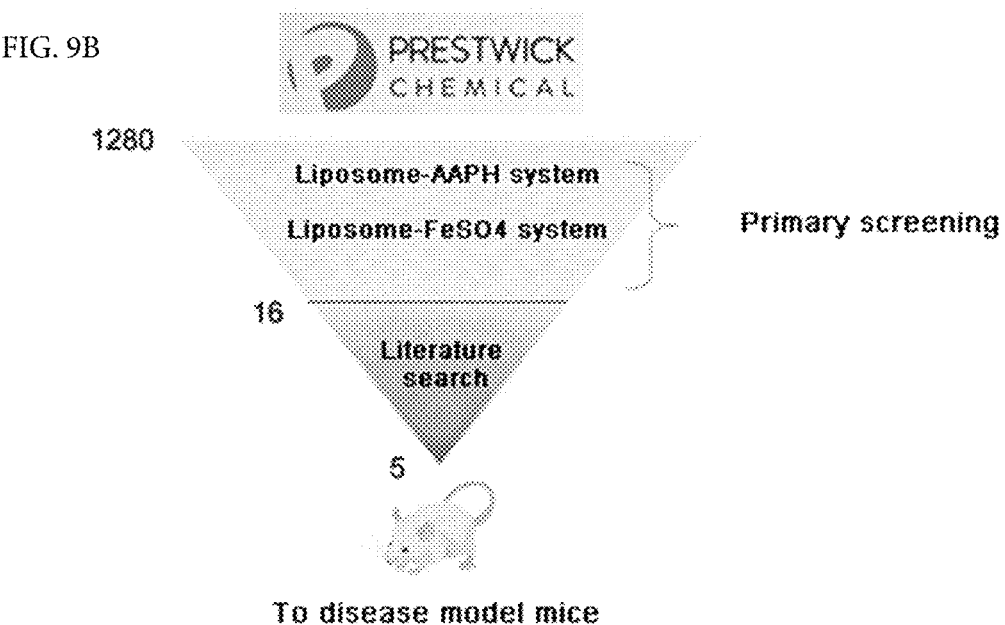

Here, the compound library may or may not be a known one. Examples of the known compound library include compound libraries that collect compounds that have already been approved as food (for example, by U.S. Food and Drug Administration (FDA)) or as pharmaceutical (for example, by European Agency for the Evaluation of Medicinal Products (EMEA)) (for example, the PRESTWICK CHEMICAL library, which is the collection of compounds with expired patent term), and compound libraries that collect compounds that have not yet been approved as food or pharmaceutical (for example, Core Library in the General Library of Drug Discovery Initiative, the University of Tokyo,). A schematic diagram of the screening method of the present invention is shown in FIGS. 9A-FIG. 9B.

Primary Screening

In the screening by the liposome-AAPH system assay method, compounds having a radical scavenging ability, ranging from highly water-soluble antioxidants that inhibit water-soluble AAPH-derived radical species to highly lipid-soluble antioxidants that inhibit lipid peroxidation chain reactions can be detected. In addition, in the screening by the liposome-$Fe^{2+}$ system assay method, more lipophilic compounds among the compounds with radical scavenging ability are more easily detected. However, iron chelating agents without radical scavenging ability may be detected. Thus, in this primary screening, first, candidate compounds having radical scavenging ability are broadly selected from test compounds by AAPH system screening, then, from the compounds narrowed down by the liposome-AAPH system screening, candidate lipid-soluble compounds are further narrowed down by liposome-$Fe^{2+}$ system screening.

The screening method using the assay method of the present invention includes, as the primary screening, a screening by the cell-free based assay method using liposomes.

The primary screening method of the present invention includes the following method: a screening method for selecting a candidate compound having high lipid peroxidation inhibitory activity, including:
i) selecting a test compound from a compound library;
ii) performing a screening using the test compound by a cell-free assay method using 2,2'-azobis(2-aminopropane) dihydrochloride (hereinafter referred to as "AAPH")(hereinafter, this assay method referred to as "liposome-AAPH system"), and selecting a compound having a high activity value; and
iii) then, performing a screening using the compound having a high activity value in ii) by a cell-free assay method using a divalent iron ion source material (hereinafter, this assay method referred to as "liposome-$Fe^{2+}$ system"), and selecting a compound having a high activity value.

From the fluorescence intensity measured in the screening of the above ii), the activity value of each test compound is calculated based on the following expression:

$$\text{Activity value} = 1 - (\text{Flu}_{Sample} - \text{Flu}_{Background})/(\text{Flu}_{Control} - \text{Flu}_{Background})$$

$\text{Flu}_{Sample}$: Fluorescence intensity for with AAPH and with each compound (n=1)
$\text{Flu}_{Background}$: Fluorescence intensity for without AAPH
$\text{Flu}_{Control}$: Fluorescence intensity for with AAPH and without each compound From the fluorescence intensity measured in the screening of the above iii), the activity value of each test compound is calculated based on the following expression:

$$\text{Activity value} = 1 - (\text{AUC}_{Sample}/\text{AUC}_{Control})$$

$\text{AUC}_{Sample}$: Area under the curve calculated from the fluorescence intensity for with $Fe^{2+}$ and with each compound (n=1)
$\text{AUC}_{Control}$: Area under the curve calculated from the fluorescence intensity for with $Fe^{2+}$ and without each compound.

Narrowing of candidate compounds is performed in comparison with the activity value of known compounds which have been known to have high lipid peroxidation inhibitory activity (hereinafter referred to as "activity indicator compounds"). Examples of the activity indicator compound include Edaravone, 4-hydroxy-2,2,6,6-tetramethylpiperidin-1-oxyl (Tempol) and (−)-epicatechin.

Secondary Screening

When using a compound library that collects compounds unapproved as food or pharmaceutical (for example, Core Library in the General Library of Drug Discovery Initiative, the University of Tokyo,) as the compound library, the screening using the assay method of the present invention may employ a screening by the cell-based assay method of the present invention using a cultured cell (for example, human hepatoma-derived HepG2 cell), as higher-order screening (for example, secondary screening), for the purpose of investigating lipid peroxidation inhibitory activity and cell death inhibitory activity in a cell system. On the other hand, when using a compound library that collects compounds already approved as food or pharmaceutical, there is no need to investigate lipid peroxidation inhibitory activity and cell death inhibitory activity in the cell system, thus the secondary screening may be omitted accordingly.

In the screening for investigating lipid peroxidation inhibitory activity in the cell system, a screening is performed by the cell-based assay method of the present invention, and activity values are determined based on the results of measuring the fluorescence intensity. Then, candidate compounds are narrowed down in comparison with the activity value of the activity indicator compound.

The secondary screening method of the present invention includes a method including:
i) performing a screening by a cell-based assay method using arachidonic acid, and selecting a compound having a high activity value;
ii) performing a cell-based assay method using tert-butyl hydroperoxide, and selecting a compound having a high activity value; and
iii) selecting a compound having high activity values in both of the assay methods of i) and ii).

In the screening by the cell-based assay method, activity values were determined from the values of fluorescence intensity measured in each screening using AA or tBHP as a reaction initiator, based on the following expression:

Activity value=$100(AUC_{Sample}-AUC_{Background})/(AUC_{Control}-AUC_{Background})$ $AUC_{Sample}$: Area under the curve calculated from the fluorescence intensity for with reaction initiator and with each compound (n=1)
$AUC_{Control}$: Area under the curve calculated from fluorescence intensity for with reaction initiator and without each compound
$AUC_{Background}$: Area under the curve calculated from fluorescence intensity for without reaction initiator and without each compound Then, the candidate compounds are narrowed down in comparison with the value of the activity indicator compound. The activity values obtained in each screening using AA or tBHP are plotted. Candidate compounds having high activity values for lipid peroxidation inhibition in both of the screenings are selected.

Moreover, compounds which have high lipid peroxidation-induced cell death inhibitory activity are explored.

As a cell-based screening for examining the cell death inhibitory activity, an assay using human hepatoma-derived HepG2 cells and AA and tBHP as radical initiators is performed, and the cell viability is measured. The activity value is determined from the cell viability value based on the following expression:

Activity value=$100(\text{Viability}_{Sample}-\text{Viability}_{Control(+)})/(\text{Viability}_{Control(-)}-\text{Viability}_{Control(+)})$ $\text{Viability}_{Sample}$: Cell viability for with reaction initiator and with each compound (n=1)
$\text{Viability}_{Control(+)}$: Cell viability for with reaction initiator and with each compound
$\text{Viability}_{Control(-)}$: Cell viability for without reaction initiator and without each compound Then, the candidate compounds are narrowed down in comparison with the value of the activity indicator compound. The activity values obtained in each assay system using AA or tBHP are plotted. Candidate compounds having high activity values for cell death inhibition (cell death suppression) in both of the assay systems are selected.

In one embodiment, the secondary screening method of the present invention further includes a method including:
i) performing a screening by an assay method according to an MTT method using a culture medium containing a cultured cell, a test compound, and arachidonic acid, and selecting a compound having high cell viability;
ii) performing a screening by an assay method according to an MTT method using a culture medium containing a cultured cell, a test compound, and tert-butyl hydroperoxide, and selecting a compound having high cell viability; and
iii) selecting a candidate compound having high cell viability in both of the assay methods of i) and ii).

Tertiary Screening

The compound library to be used (for example, Core Library of Drug Discovery Initiative, the University of Tokyo,) may include, for example, structural analogs related to candidate compounds that have high activity values in the above-described low-order screening assays (for example, secondary screening). Thus, by performing higher-order screening (for example, tertiary screening) of such structural analogs, optionally, together with the candidate compound selected in the low-order screening assays for lipid peroxidation inhibitory activity, candidate compounds are selected.

Moreover, these candidate compounds are further screened by an assay method for examining cell death inhibitory activity.

Finally, a candidate compound is chosen entirely taking into account the result of the final high-order screening (for example, tertiary screening) and the result of the screening for cell death inhibitory activity.

In one embodiment, the screening method of the present invention includes:
i) selecting a structural analog of a compound selected by a screening method by the cell-based assay of the present invention from a compound library;
ii) performing the screening method by the cell-based assay of the present invention for the compound selected in i) and optionally the original compound of the selection, and selecting a compound having a high activity value;
iii) performing the screening method by the cell-based assay of the present invention according to an MTT method for the compound selected in i) and optionally the original compound of the selection, and selecting a compound having high cell viability;
iv) selecting a candidate compound having a high activity value and high cell viability in the screening methods of ii) and iii) and
v) performing a screening by an assay method using a culture medium containing a cultured cell for the compound selected in i) and optionally a compound selected by screening by the cell-based assay or screening by the cell assay according to an MTT method, and selecting a candidate compound having a high cell viability; and
vi) selecting a candidate compound from the compound selected in iv) and the compound selected in v).

The screening method of the present invention can be used as a high-throughput screening method.

(Utilization of Screening Results)

Diseases involving lipid radicals in lipid peroxidation reactions cover a wide range of disease areas. Thus, candidate compounds can be narrowed down for each target disease in consideration of other factors based on the knowledge of the action mechanism. For example, when targeting a disease requiring permeability to the blood-brain barrier, candidate compounds may be further narrowed down considering lipid solubility. Specifically, when targeting cerebral infarction and retinal diseases (for example, age-related macular degeneration), compounds that are permeable to the blood brain barrier are advantageous, while when targeting hepatoma and arteriosclerosis, permeability to the blood brain barrier is not required.

(Medical Use)

As used herein, "treating" or "preventing" a disease caused by lipid peroxidation reaction encompasses one or more of the followings: (1) removing the disease; (2) reducing or minimizing the severity of the disease; (3) delaying the progression or onset of the disease; and (4) reducing, minimizing, or eliminating the occurrence or frequency of the disease.

As used herein, "disease caused by a lipid peroxidation reaction" or "lipid peroxidation reaction-induced disease" includes diseases where the association of the disease with the lipid peroxidation reaction is known, for example, as shown in FIG. 1. Examples of the diseases include one or more diseases selected from the group consisting of Alzheimer-type dementia, chronic kidney diseases, diabetic neuropathy, liver disorder, age-related macular degeneration, postischemic brain disorder, vascular dementia, arteriosclerosis, Parkinson's disease, multiple sclerosis, cancer, asthma, hypertension, cardiovascular diseases, and age-related eye disease.

As used herein, the "subject" includes human or non-human animals.

The active drug of the present invention includes a pharmaceutically acceptable salt thereof. In addition, the active drug of the present invention or a pharmaceutically acceptable salt thereof includes a hydrate or a solvate thereof with a solvent or the like. The present invention also includes any form of crystal of the active drug of the present invention.

Examples of the pharmaceutically acceptable salt include salts with organic bases (for example, diethanolamine salts, ethylenediamine salts), and salts with inorganic bases (for example, salts with alkali metals (for example, sodium, potassium) and salts with alkaline earth metals (for example, calcium, or magnesium).

The active drug of the present invention can be administered orally or parenterally (for example, intravenously, subcutaneously, or intramuscularly, topically, rectally, transdermally, intraspinally, or nasally) as a pharmaceutical composition when used for treatment or prevention. Examples of compositions for oral administration include tablets, capsules, pills, granules, powders, solutions, and suspensions. Examples of compositions for parenteral administration include aqueous or oily injectables, ointments, creams, lotions, aerosols, suppositories, and patches. These formulations are prepared using conventionally known techniques and can contain a non-toxic and inert carrier or additive (hereinafter referred to as "pharmaceutically acceptable carrier") which is usually used in the pharmaceutical field.

As used herein, "pharmaceutically acceptable carrier" may include, in addition to the effective active ingredient, various active ingredients or medicinal ingredients (including pharmacological active ingredients and physiologically active ingredients) and additives (for example, buffering agents, isotonic agents, pH adjusters, antiseptics/preservatives, stabilizers, viscosity enhancing agents, chelating agents, surfactants, fragrances) in combination, according to various uses, as long as the pharmacological effect or the like is not hindered. Such ingredients can be appropriately mixed within a concentration range that does not cause problems such as stimulation. The kinds of ingredients are not particularly limited, but examples of them include buffering agents (for example, sodium phosphate), isotonic agents (for example, sodium chloride), pH adjusting agents (for example, boric acid), antiseptics/preservatives (for example, benzalkonium chloride), stabilizers (for example, mannitol), viscosity enhancing agents (for example, sodium alginate), chelating agents (for example, sodium edetate), surfactants (for example, polyoxyethylene sorbitan monooleate), and fragrances (for example, menthol).

As used herein, the term "administering" means that an active drug or pharmaceutical composition containing it is provided and/or prescribed to an individual of subject, or the individual receives an active drug or pharmaceutical composition of the present invention. The route of administration of the active drug or pharmaceutical composition of the present invention can be any route of administration, and can vary depending on intended disease, symptom, age, weight or sex of the subject, or the like.

As used herein, an "effective amount" means an amount of an active drug sufficient to provide the desired effect, that is, treatment or prevention of the lipid peroxidation reaction-induced diseases described herein. The active drug or the pharmaceutical composition of the present invention may be used in combination with a known active drug or a pharmaceutical composition for the intended disease.

The dose of the active drug of the present invention varies depending on the individual active drug or the pharmaceutical composition, and also depending on the disease, age, weight, sex, or symptom of the subject, route of administration, or the like. In the case of parenteral administration, the dose is usually 0.001 to 100 mg/kg, preferably 0.01 to 100 mg/kg per day. In the case of oral administration, the dose is usually 0.01 to 1000 mg/kg, preferably 0.1 to 100 mg/kg per day. The active drug of the present invention is administered once or multiple times (or two or three times) a day. It can also be administered once every several days to several weeks.

EXAMPLES

Examples of the present invention will be described below as Examples, but the present invention is not limited thereto.

Reagents, cell culture-related reagents, and profluorescent nitroxide compounds were obtained commercially or manufactured according to known methods. Core Library compounds and Prestwick Chemical Library compounds were provided from Drug Discovery Initiative, the University of Tokyo, and the Kyushu University Compound Library Drug Discovery Advanced Research and Education Platform Center, respectively. Commonly used instruments were employed as various instruments in the measurement.

Reference Example 1

Production of NBD-TEMPO Compound 2,2,6,6-Tetramethyl-4-(4-nitrobenzo[1,2,5]oxadiazol-7-ylamino)piperidin-1-oxyl (NBD-TEMPO) was prepared according to the following procedure. Specifically, 366 mg (2.0 mmol) of 4-fluoro-7-nitro-2,1,3-benzoxadiazole was dissolved in 10 mL of AcOEt, and to the resulting solution, 342 mg (2.0 mmol) of 4-amino-2,2,6,6-tetramethylpiperidin-1-oxyl was added. After stirring the mixture at room temperature for 3 hours, saturated saline was added, and the resulting mixture was extracted with AcOEt. The organic layer was dried over $Na_2SO_4$ and the solvent was completely distilled off. Then, the residue was purified by silica gel column chromatography ($CHCl_3$) to obtain 574 mg of orange yellow crystal (yield: 86%). HRMS($ESI^+$) cald for $C_{15}H_{20}N_5NaO_4$ $[M+Na]^+$: 357.1413, found: 357.1415.

Reference Example 2

Production of Dansyl-TEMPO Compound 2,2,6,6-Tetramethyl-4-(5-(dimethylamino)naphthalene-1-sulfonylamino)piperidin-1-oxyl (Dansyl-TEMPO) was produced according to the method described in the literature (for example, by Lozinsky et al.: Lozinsky, E., et. al., J. Biolchem. Biophys., Methods, 1999, 38, 29-42). Specifically, 1.03 g (6.0 mmol) of 4-amino-2,2,6,6-tetramethylpiperidin-1-oxyl was dissolved in 5 ml of acetone, and to the resulting solution, 1.35 g (5.0 mmol) of 5-(dimethylamino) naphthalene-1-sulfonyl chloride and 0.483 ml of pyridine were added in an ice bath. After stirring the mixture at room temperature overnight, saturated saline was added, and the resulting mixture was extracted with diethyl ether. The organic layer was dried over $Na_2SO_4$ and the solvent was completely distilled off. Then, the residue was separated and purified by silica gel column chromatography ($CHCl_3$:

MeOH=99:1) to obtain 396 mg of the product (yield: 20%). HRMS(ESI$^+$) cald for $C_{21}H_{30}N_3NaO_3S$ [M+Na]$^+$: 427.1906, found: 427.1900.

Reference Example 3

Production of NBD-TEEPO Compound 2,2,6,6-tetraethyl-4-(4-nitrobenzo[1,2,5]oxadiazol-7-ylamino)piperidin-1-oxyl (NBD-TEEPO) was produced according to the method described in the literature (for example, by Bognar et al.: Bognar, B., et al., J. Heterocycl. Chem., 2006, 43, 81-86). Specifically, 87.6 mg (0.44 mmol) of 4-chloro-7-nitro-2,1,3-benzoxadiazole and 61 µL of Et$_3$N was dissolved in 10 mL of AcOEt, and to the resulting solution, 100 mg (0.44 mmol) of 4-amino-2,2,6,6-tetraethylpiperidin-1-oxyl was added. After stirring the mixture at room temperature for 6 hours, saturated saline was added, and the resulting mixture was extracted with AcOEt. The organic layer was dried over Na$_2$SO$_4$ and the solvent was completely distilled off. Then, the residue was separated and purified by silica gel column chromatography (Hexane:AcOEt=100:0 to 70:30) to obtain 83 mg of orange yellow crystal (yield: 6%). HRMS(ESI$^+$) cald for $C_{19}H_{28}N_5NaO_4$ [M+Na]$^+$: 413.2034, found: 413.2024.

Reference Example 4

Production of NBD-Pen Compound

Similar to the synthesis method of 2,2,6,6-tetraethyl-4-(4-nitrobenzo[1,2,5]oxadiazol-7-ylamino)piperidin-1-oxyl (NBD-TEEPO), but replacing 100 mg (0.44 mmol) of 4-amino-2,2,6,6-tetraethylpiperidin-1-oxyl (4) with 100 mg (0.44 mmol) of 4-amino-2,2,6-trimethyl-6-pentylpiperidin-1-oxyl (8), the reaction was carried out. The product was separated and purified by silica gel column chromatography (Hexane:AcOEt=100:0 to 70:30) to obtain 83 mg of orange yellow crystal (yield: 48%). HRMS(ESI$^+$) cald for $C_{19}H_{28}N_5NaO_4$ [M+Na]$^+$: 413.2034, found: 413.2056.

Example 1

Evaluation of Responsiveness of Profluorescent Nitroxide Probe to Lipid Peroxidation Reaction In a phosphate buffer (10 mM, pH 7.4, 0.5% DMSO, 0.5% acetonitrile), profluorescent nitroxide (NBD-TEMPO compound or Dansyl-TEMPO compound) (5.0 µM) and liposomes (2.5 mg/mL Egg PC, 0.1 mg/mL DCP) were mixed at 37° C. AAPH (20 mM) was added to the mixture, and the lipid peroxidation reaction was started. After 40 minutes, the fluorescence intensity was measured at an excitation wavelength of 470 nm and a fluorescence wavelength of 530 nm for NBD-TEMPO, and at an excitation wavelength of 300 nm and a fluorescence wavelength of 500 nm for Dansyl-TEMPO.

The results are shown in FIG. 2.

When the prepared liposomes were stimulated with addition of AAPH, the fluorescence intensity of NBD-TEMPO increased 8.2 times compared to that in the case without AAPH, while the fluorescence intensity of Dansyl-TEMPO increased only 1.4-fold. Thus, the NBD group was employed as the fluorophore.

Example 2

Evaluation of Reactivity of Profluorescent Nitroxide Probe with Various Reductants Profluorescent nitroxides (5.0 µM) (NBD-TEMPO compound, NBD-Pen compound, or NBD-TEEPO compound) and 50 µM of various reductants (AsA, UA, TPL, Eda, Catechin, Trolox) were mixed in phosphate buffer (10 mM, pH 7.4, 0.5% DMSO, 0.5% acetonitrile) containing liposomes (2.5 mg/mL Egg PC, 0.1 mg/mL DCP) at 37° C. Lipid peroxidation reaction was caused by adding AA (0.5 mM) and LOX (25 µg/mL). After 40 minutes, the fluorescence intensity was measured at an excitation wavelength of 470 nm and a fluorescence wavelength of 530 nm. Here, AsA means ascorbic acid, UA means uric acid, TPL means 2,2,6,6-tetramethylpiperidin-1-oxyl, Eda means Edaravone, catechin means (−)-epicatechin, and Trolox means 6-hydroxy-2,5,7,8-tetramethylchroman-2-carboxylic acid.

The results are shown in FIGS. 3A-FIG. 3B.

As model antioxidants, the following six compounds were selected (FIG. 3A). AsA, which acts as a water-soluble antioxidant in human body and is also included in many foods or the like; Uric acid, the most abundant antioxidant in human blood; 4-hydroxy-2,2,6,6-tetramethylpiperidyl-1-oxyl (Tempol), a compound which is widely used in research using laboratory animal models among nitroxide compounds due to its low toxicity; Edaravone (Eda), which is approved as a free radical scavenger; Catechin ((−)-epicatechin), which is included in tea, wine or the like, and commonly consumed; and Trolox, an analog compound of VitE. It is known that the water-octanol partition coefficients (Log Po/w) of these six compounds are high in the order of AsA<UA<TPL<Eda<Catechin<Trolox.

When the NBD-TEMPO compound was used, the fluorescence intensity increased about 7.7 times by the reaction with AsA, and when the NBD-Pen compound was used, the fluorescence intensity increased about 2.9 times by the reaction with Eda. However, when the NBD-TEEPO compound was used, the fluorescence intensity had little increase (FIG. 3B).

Example 3

Evaluation of Reactivity of Profluorescent Nitroxide Probe with Various Oxidants Profluorescent nitroxides (NBD-TEMPO compound, NBD-Pen compound, or NBD-TEEPO compound) (5.0 µM) and various oxidants were mixed in phosphate buffer (10 mM, pH 7.4, 0.5% DMSO, 0.5% acetonitrile) at 37° C. Hydrogen peroxide, hypochlorous acid, and potassium oxide (0.5 mM each) were used as the oxidants. •OH was generated with hydrogen peroxide (0.5 mM) and FeSO$_4$ (5.0 µM). Lipid radicals were generated by liposomes (2.5 mg/mL Egg PC, 0.1 mg/mL DCP) and AAPH (10 mM). After 30 minutes, fluorescence intensity was measured at an excitation wavelength of 470 nm and a fluorescence wavelength of 530 nm.

Figure 4:
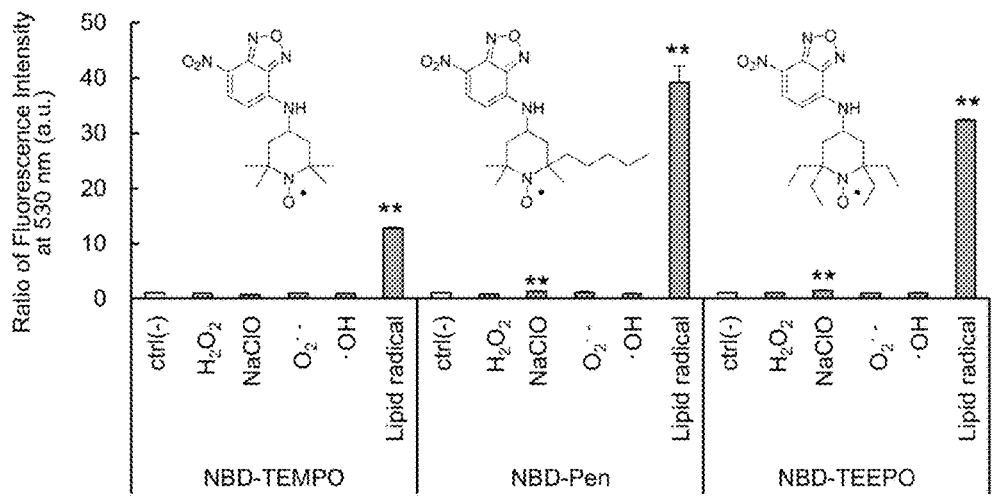
FIG. 4 is a chart showing the result of a test for evaluating the reactivity between profluorescent nitroxide probes and various oxidants. 5.0 μM profluorescent nitroxide and various oxidants were mixed, and after 30 minutes, the fluorescence intensity ($\lambda_{Ex}/\lambda_{Em}$=470/530 nm) was measured. The ratio of fluorescence intensity is a value obtained by dividing the fluorescence intensity of the probe after reaction with the various oxidants by the fluorescence intensity of ctrl(−). As the oxidants, 0.5 mM hydrogen peroxide, 0.5 mM hypochlorous acid, 0.5 mM potassium oxide, 0.5 mM hydrogen peroxide and 5.0 μM $FeSO_4$ were used, and liposomes (2.5 mg/mL EggPC, 0.1 mg DCP) and 10 mM AAPH were used (n=3, mean+S.D., **p<0.01 v.s. ctrl(−)).

The results are shown in FIG. 4.

Any probe molecules showed little increase of the fluorescence intensity by reaction with ROS. The NBD-TEMPO compound had the lowest responsiveness to lipid peroxidation reaction, thus it was found that the NBD-TEEPO and NBD-Pen compounds have advantages in responsiveness to lipid peroxidation reaction.

From the above results, it was decided that the NBD-TEEPO compound which showed the highest reduction resistance and high responsiveness to lipid peroxidation reaction be employed.

Example 4

Evaluation of Reaction Initiator Concentration-Dependent Lipid Peroxidation in Artificial Lipid Membranes (NBD-TEEPO Assay)

Probes (NBD-TEEPO compound) (5.0 µM) and liposomes (2.5 mg/mL Egg PC, 0.1 mg/mL DCP) were mixed in phosphate buffer (10 mM, pH 7.4, 0.5% DMSO, 0.5% acetonitrile) at 37° C. AAPH (0-20 mM) or $FeSO_4$ (0-2.0 mM) was added to the mixture, and the lipid peroxidation reaction was started. After 40 minutes in the AAPH system or after 60 minutes in the $Fe^{2+}$ system, the fluorescence intensity was measured at an excitation wavelength of 470 nm and a fluorescence wavelength of 530 nm.

The results are shown in FIG. 5A-FIG. 5D 5 (AAPH) and FIGS. 6A-FIG. 6D ($FeSO_4$).

Figure 5A:
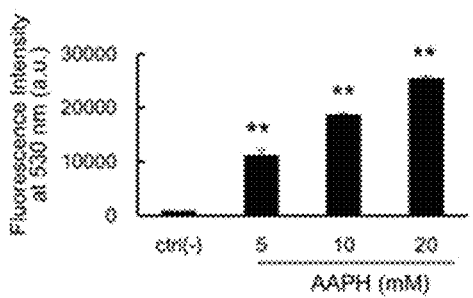
FIGS. 5A-FIG. 5D is charts showing the results of a test for evaluating the reaction initiator concentration-dependent lipid peroxidation reaction in artificial lipid membranes in an AAPH system. Liposomes (2.5 mg/mL EggPC, 0.1 mg DCP), 5.0 μM NBD-TEEPO, and AAPH were mixed, and after 40 minutes, the fluorescence intensity ($\lambda_{Ex}/\lambda_{Em}$=470/530 nm) was measured.
Figure 5B:
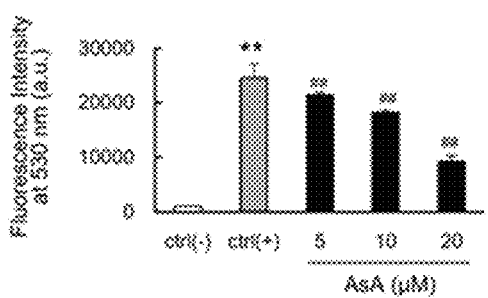
Figure 5C:
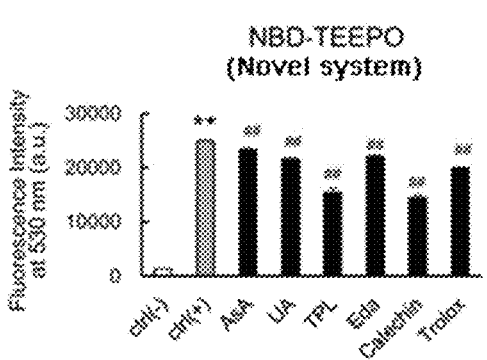
Figure 5D:
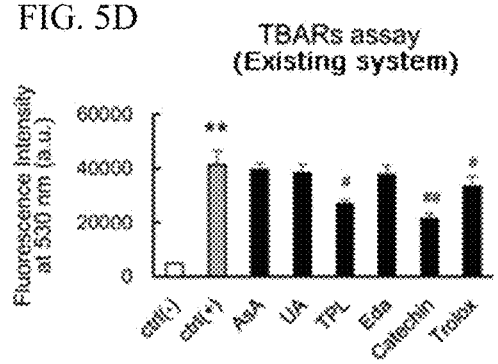
Figure 6A:
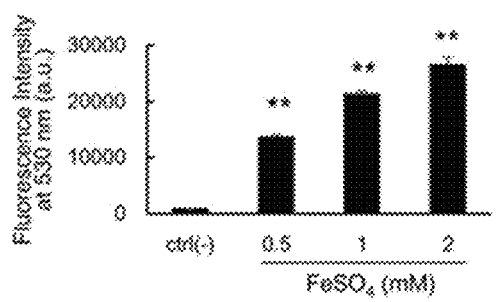
FIGS. 6A-FIG. 6D is charts showing the results of a test for evaluating the reaction initiator concentration-dependent lipid peroxidation reaction in artificial lipid membranes in an $Fe^{2+}$ system. Liposomes (2.5 mg/mL EggPC, 0.1 mg DCP), 5.0 μM NBD-TEEPO and $FeSO_4$ were mixed, and after 60 minutes, the fluorescence intensity ($\lambda_{Ex}/\lambda_{Em}$=470/530 nm) was measured.
Figure 6B:
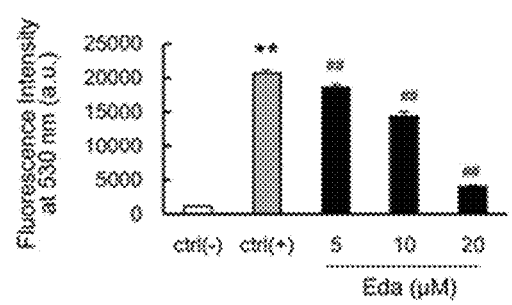
Figure 6C:
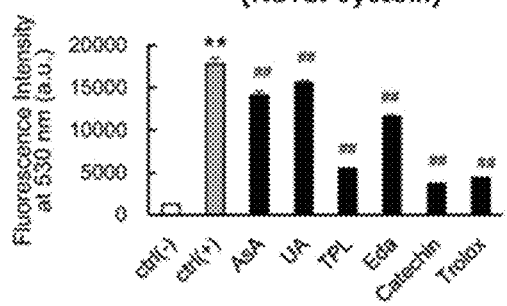
Figure 6D:
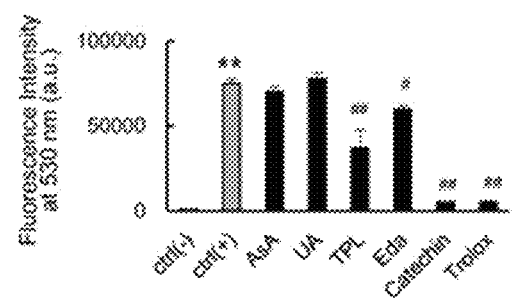
Figure 8E:
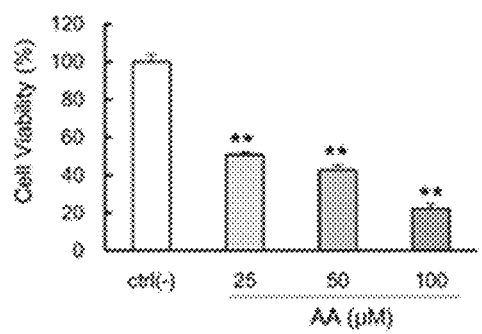
Figure 8E:
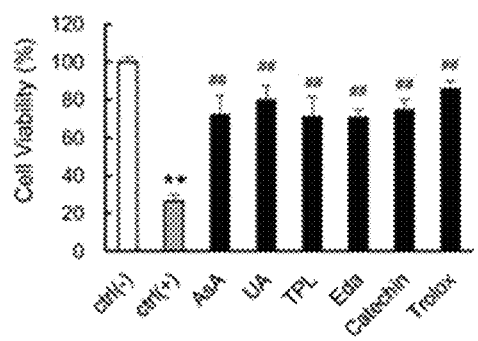
Figure 8E:
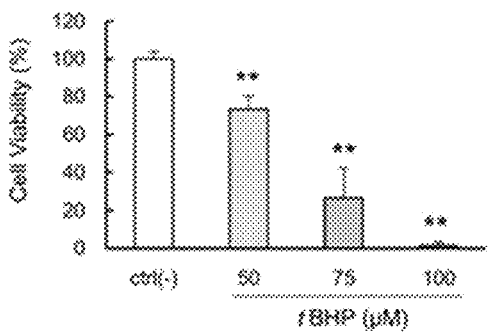
Figure 8E:
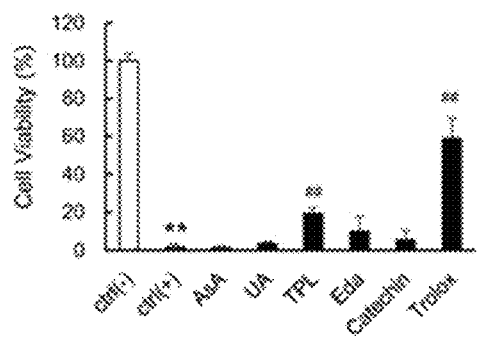

The fluorescence intensity of the probe increased concentration-dependently in both of the AAPH and $Fe^{2+}$ systems (FIG. 5A and FIG. 6A). Addition of water-soluble AsA in the AAPH system or lipid-soluble antioxidant Eda in the $Fe^{2+}$ system inhibited the fluorescence increase concentration-dependently (FIG. 5B and FIG. 6B). Thus, the lipid peroxidation inhibitory effects of six typical antioxidants were measured. When compared the measurement result with the result of the TBARS method, an existing method shown in Example 5 (FIG. 5D and FIG. 6D), both showed the same tendency (FIG. 5C and FIG. 6C).

For the cell-free based assay system using AAPH or $Fe^{2+}$, the S/B ratios, CV values, and Z'-factors, which represent the quality of assay system, were examined using the NBD-TEEPO compound. The results are shown in the table below. All indicators exceeded the target values (Table 1).

TABLE 1

| Indicators | AAPH system | $Fe^{2+}$ system | Target value |
| --- | --- | --- | --- |
| S/B ratio | 18.7 | 8.7 | 2 or more |
| CV value of Background (%) | 4.9 | 3.2 | 10% or less |
| CV value of Control(%) | 5.4 | 3.2 | 10% or less |
| Z'-factor | 0.82 | 0.88 | 0.5 or more |

Example 5

Evaluation of Lipid Peroxidation Inhibition by Antioxidants in Artificial Lipid Membranes (TBARS Assay)

Various reductants (10 µM) and liposomes (2.5 mg/mL Egg PC, 0.1 mg/mL DCP) were mixed in phosphate buffer (10 mM, pH 7.4, 0.5% DMSO, 0.5% acetonitrile) at 37° C. AAPH (20 mM) or $FeSO_4$ (1.0 mM) was added to the mixture, and the lipid peroxidation reaction was started. After 60 minutes, the lipid peroxidation reaction was stopped by BHT (10 mM). Acetic acid (5.7%), TBA (0.56%), and SDS (1.07%) were added, and after stirring, the mixture was allowed to react at 60° C. for 60 minutes. The resultant was subjected to centrifugation (2000 rpm, 4° C., 15 minutes), and the fluorescence intensity was measured at an excitation wavelength of 512 nm and a fluorescence wavelength of 553 nm.

In the same manner as in Example 4, lipid peroxidation inhibition effects of the six typical antioxidants were measured.

The results are shown in FIGS. 5A-FIG. 5D (AAPH) and FIG. 6A-FIG. 6D ($FeSO_4$). The lipid peroxidation inhibitory effects shown in the Figures had a similar tendency to the result of Example 4.

Example 6

Cell Culturing

Human hepatoma cells (HepG2 cells) were cultured with DMEM medium (containing 10% FBS, 1% Penicillin-Streptomycin and 1×MEM non-essential amino acids) in a $CO_2$ incubator (37° C., 5% $CO_2$). Passaging was performed when 60-70% subconfluent state was reached. DMEM media (phenol red free, containing 1% Penicillin-Streptomycin) was used for various measurements.

Example 7

Evaluation of Reaction Initiator Concentration-Dependent Intracellular Lipid Peroxidation Reaction (NBD-TEEPO Assay)

HepG2 cells were seeded in a 96-well plate at 10,000 cells/well. The cells were incubated for 24 hours to adhere. AA (0 to 200 µM) or tBHP (0 to 300 µM), and probe (5.0 µM) were added to the cells in DMEM medium (0.5% DMSO, 0.5% acetonitrile), and after 45 minutes, the fluorescence intensity was measured at an excitation wavelength of 470 nm and a fluorescence wavelength of 530 nm.

Example 8

Evaluation of Intracellular Lipid Peroxidation Inhibition by Antioxidants (NBD-TEEPO Assay)

HepG2 cells were seeded in a 96-well plate at 10,000 cells/well. The cells were incubated for 24 hours to adhere. AA (200 µM) or tBHP (0 to 300 µM), antioxidant (50 µM), and probe (5.0 µM) were added to the cells in DMEM medium (0.5% DMSO, 0.5% acetonitrile), and after 45 minutes, the fluorescence intensity was measured at an excitation wavelength of 470 nm and a fluorescence wavelength of 530 nm.

The results are shown in FIGS. 7A-FIG. 7E.

AA and tBHP concentration-dependent fluorescence increases were observed (FIG. 7A and FIG. 7C). Furthermore, addition of antioxidants inhibited the increase (FIG. 7B and FIG. 7D). Catechin showed the strongest inhibitory effect, and the inhibitory effect had the same tendency regardless of the reaction initiator.

Example 9

Evaluation of Changes in Reaction Initiator Concentration-Dependent Cell Viability (MTT Assay)

HepG2 cells were seeded in a 96-well plate at 10,000 cells/well. The cells were incubated for 24 hours to adhere. AA (0 to 100 µM) or tBHP (0 to 100 µM) were added to the cells in DMEM medium (0.5% DMSO, 0.5% acetonitrile), and after 24 hours, the medium was exchanged. MTT solution (0.5 mg/mL, 0.5% DMSO) was added, and then the cells were incubated for 4 hours, and the solution was removed. 100 µL of DMSO was added, and the absorbance at 630 nm was measured. The cell viability was calculated with regarding the case without AA or tBHP as 100%.

Example 10

Evaluation of Changes in Cell Viability by Antioxidants (MTT Assay)

HepG2 cells were seeded in a 96-well plate at 10,000 cells/well. The cells were incubated for 24 hours to adhere. AA (200 µM) or tBHP (0 to 300 µM), and antioxidant (50 µM) were added to the cells in DMEM medium (0.5% DMSO, 0.5% acetonitrile), and the medium was changed after 24 hours. MTT solution (0.5 mg/mL, 0.5% DMSO) was added, and the cells were incubated for 4 hours, then the solution was removed. 100 µL of DMSO was added, and the absorbance at 630 nm was measured. The cell viability was calculated with regarding the case without AA or tBHP as 100%.

The results are shown in FIGS. 8A-FIG. 8E.

By the addition of AA and tBHP, the cell viability decreased concentration-dependently (FIG. 8A and FIG. 8C). Furthermore, the effect was inhibited by antioxidants (FIG. 8B and FIG. 8D). Depending on the reaction initiators, there were different tendencies in the antioxidants having high inhibitory effect.

For the cell-based assay system using AA or tBHP, the S/B ratios, CV values, and Z'-factors, which represent the quality of assay system, were examined using the NBD-TEEPO compound or MTT. The results are shown in Tables 2 and 3 below. All indicators exceeded the target values.

TABLE 2

| | NBD-TEEPO compound | | |
|---|---|---|---|
| Indicators | AA system | tBHP system | Target value |
| S/B ratio | 4.1 | 2.2 | 2 or more |
| CV value of Background (%) | 6.5 | 3.8 | 10% or less |
| CV value of Control (%) | 2.8 | 5.0 | 10% or less |
| Z'-factor | 0.83 | 0.62 | 0.5 or more |

TABLE 3

| | MTT method | | |
|---|---|---|---|
| Indicators | AA system | tBHP system | Target value |
| S/B ratio | 25.0 | 6.3 | 2 or more |
| CV value of Background (%) | 4.7 | 6.9 | 10% or less |
| CV value of Control (%) | 4.8 | 6.9 | 10% or less |
| Z'-factor | 0.85 | 0.71 | 0.5 or more |

Example 11

Primary Screening Using Core Library of Drug Discovery Initiative, the University of Tokyo (AAPH System)

For the compounds, 2 mM 100% DMSO solutions (dispensed at 0.125 µL/well) were provided from Drug Discovery Initiative, the University of Tokyo. Solution A containing liposomes (5.0 mg/mL Egg PC, 0.2 mg/mL DCP) and probe (10 µM) in phosphate buffer (10 mM, pH 7.4, 1.0% acetonitrile) and Solution B containing AAPH (40 mM) in phosphate buffer (10 mM, pH 7.4) were prepared. 12.5 µL each of solutions A and B were dispensed with Multidrop Combi. The final concentration was liposomes (2.5 mg/mL Egg PC, 0.1 mg/mL DCP), 5.0 µM NBD-TEEPO compound, 50 µM test compound and 20 mM AAPH in phosphate buffer (10 mM, pH 7.4, 0.5% acetonitrile, 0.5% DMSO). The reaction mixture was mixed at 37° C., and after 40 minutes, the fluorescence intensity at an excitation wavelength of 470 nm and a fluorescence wavelength of 530 nm was measured. The activity values of each test compound were determined according to the expression described herein.

Figure 10:
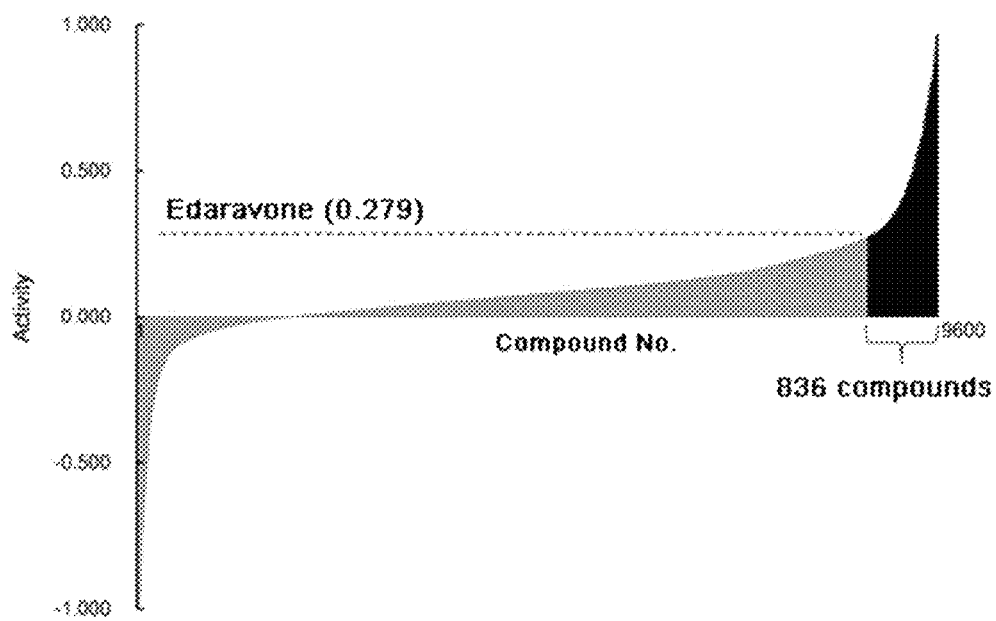
FIG. 10 is a chart showing the result of primary screening using Core Library of Drug Discovery Initiative, the University of Tokyo, in an AAPH system. Liposomes (2.5 mg/mL EggPC, 0.1 mg DCP), 5.0 μM NBD-TEEPO, and 20 mM AAPH were mixed, and the fluorescence intensity ($\lambda_{Ex}/\lambda_{Em}$=470/530 nm) was measured. The activity values of each compound at 40 minutes after the reaction are shown.

The results are shown in FIG. 10.

Of 9600 compounds, 1858 compounds had activity values below 0, that is, did not inhibit the lipid peroxidation reaction. On the other hand, 7711 compounds inhibited the lipid peroxidation reaction, and 836 compounds of which exhibited higher activity values than the known compound Edaravone. These 836 compounds were decided as hit compounds (candidate compounds) in the primary screening, and proceeded to the evaluation in $Fe^{2+}$ system.

Example 12

Primary Screening Using Core Library of Drug Discovery Initiative, the University of Tokyo ($FeSO_4$ System)

Figure 11:
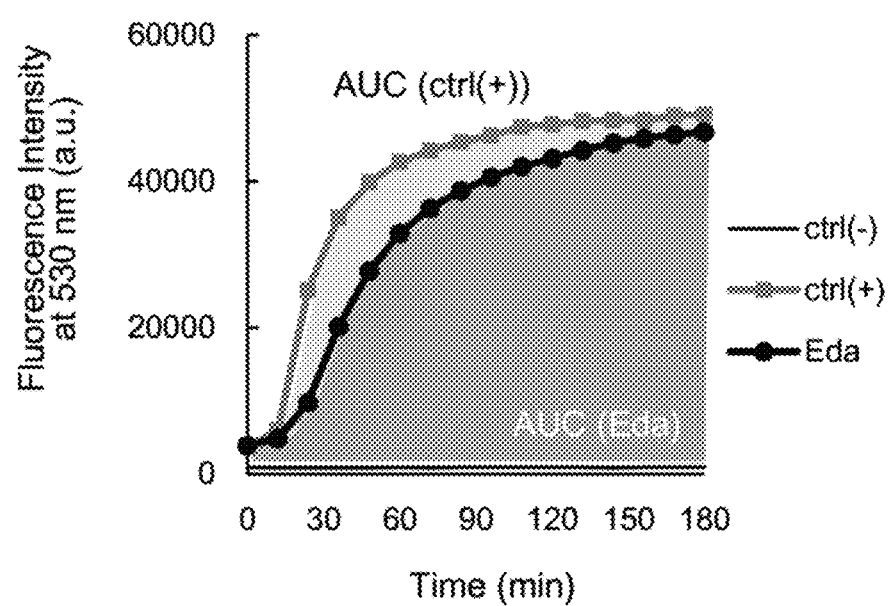
FIG. 11 is a chart showing the result of AUC evaluation in an $Fe^{2+}$ system. Liposomes (2.5 mg/mL EggPC, 0.1 mg DCP), 5.0 μM NBD-TEEPO and 1.0 mM $FeSO_4$ were mixed, and the fluorescence intensity ($\lambda_{Ex}/\lambda_{Em}$=470/530 nm) was measured over time for 180 minutes. The area under the curve (AUC) was calculated from the obtained curve.

Subsequently, evaluation was performed in $Fe^{2+}$ system for the 836 compounds that exhibited higher lipid peroxidation inhibitory effects than Edaravone in the AAPH system. For the compounds, 2 mM 100% DMSO solutions (dispensed at 0.2 µL/well) were provided from Drug Discovery Initiative, the University of Tokyo. Solution A containing liposomes (2.78 mg/mL Egg PC, 0.11 mg/mL DCP) and 5.6 µM probe in phosphate buffer (10 mM, pH 7.4, 0.56% acetonitrile) and Solution B containing 10 mM $FeSO_4$ in distilled water were prepared. Solution A was dispensed by 36 µL with Multidrop Combi. Solution B was dispensed by 4 µL with Biomek NXP. The final concentration was liposomes (2.5 mg/mL Egg PC, 0.1 mg/mL DCP), 5.0 µM probe, 50 µM test compound, 1.0 mM $FeSO_4$ in phosphate buffer (10 mM, pH 7.4, 0.5% acetonitrile, 0.5% DMSO). The reaction mixture was mixed at 37° C., and the fluorescence intensity at an excitation wavelength of 470 nm and a fluorescence wavelength of 530 nm was measured over time every 3 minutes. AUC was calculated from the fluorescence intensity for 180 minutes, and the activity value of each test compound was calculated according to the expression described herein (FIG. 11).

Figure 12:
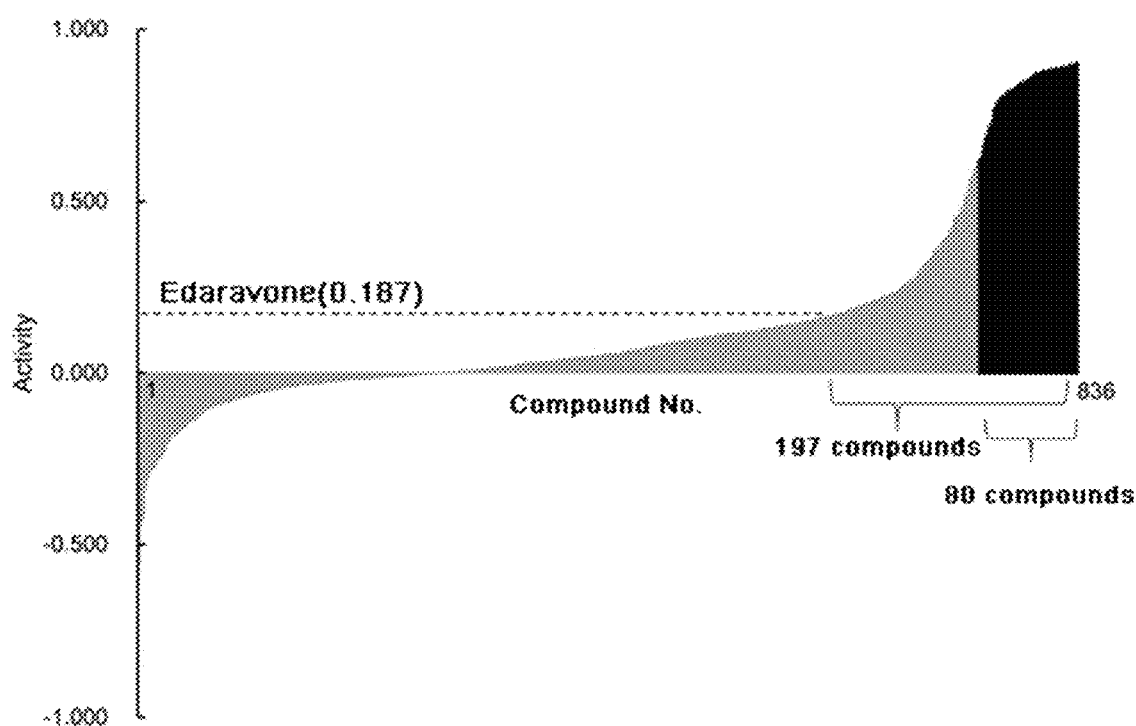
FIG. 12 is a chart showing the result of primary screening using Core Library of Drug Discovery Initiative, the University of Tokyo, in an $Fe^{2+}$ system. Liposomes (2.5 mg/mL EggPC, 0.1 mg DCP), 5.0 μM NBD-TEEPO and 1.0 mM $FeSO_4$ were mixed, and the fluorescence intensity ($\lambda_{Ex}/\lambda_{Em}$=470/530 nm) was measured. The activity values of each compound at 180 minutes after the reaction are shown.

The results are shown in FIG. 12.

Of the 836 compounds, 268 compounds had activity values below 0, that is, did not inhibit the lipid peroxidation reaction. On the other hand, 568 compounds inhibited lipid peroxidation reaction. Of these, 197 compounds showed higher activity than Edaravone. The top 80 compounds with higher inhibitory effect were decided as hit compounds (candidate compounds), and proceeded to secondary screening.

Example 13

Secondary Screening Using Core Library of Drug Discovery Initiative, the University of Tokyo (NBD-TEEPO Assay)

Secondary screening was performed for 80 compounds selected in the primary screening.

For the compounds, 10 mM 100% DMSO solutions (dispensed at 5.0 µL/well) were provided from Drug Discovery Initiative, the University of Tokyo. 495 µL of DMEM medium for measurement was added, and a 1.0% DMSO solution containing 100 µM of the compound was prepared.

This solution was dispensed by 80 µL with Biomek NXP into a measuring plate on which cells were seeded in advance. To the test compound (100 µM 1.0% DMSO), 64 µL of DMEM medium (1.25% acetonitrile) containing 12.5 µM NBD-TEEPO compound, and 16 µL of PBS in which AA (2000 µM, 5.0% ethanol) or tBHP (3000 µM) was dissolved were manually dispensed. The final concentration was 50 µM test compound and 200 µM AA or 300 µM tBHP in DMEM medium (0.5% DMSO, 0.5% acetonitrile).

The reaction mixture was mixed at 37° C., and the fluorescence intensity at an excitation wavelength of 470 nm and a fluorescence wavelength of 530 nm was measured over time every 3 minutes. The AUC was calculated from the fluorescence intensity for 45 minutes in the AA-added system or 60 minutes in the tBHP-added system, and the activity value of each test compound was calculated according to the expression described herein.

The results are shown in FIGS. 13A-FIG. 13D.

Figure 13A:
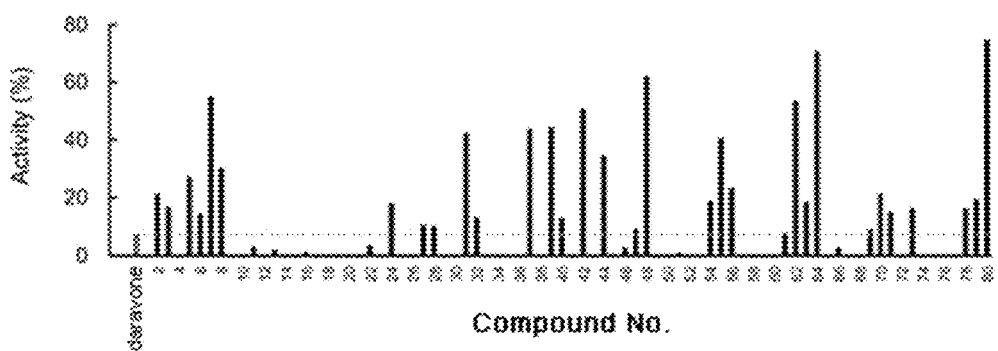
FIGS. 13A-FIG. 13D is charts showing the results of secondary screening using Core Library of Drug Discovery Initiative, the University of Tokyo. To 1.0×10$^4$ HepG2 cells, 5.0 μM NBD-TEEPO, 200 μM AA or 300 μM tBHP, and 50 μM compound were added, and changes of the fluorescence intensity ($\lambda_{Ex}/\lambda_{Em}$=470/530 nm) were measured. The dotted lines in FIG. 13A and FIG. 13B represent the activity values of Edaravone.
Figure 13B:
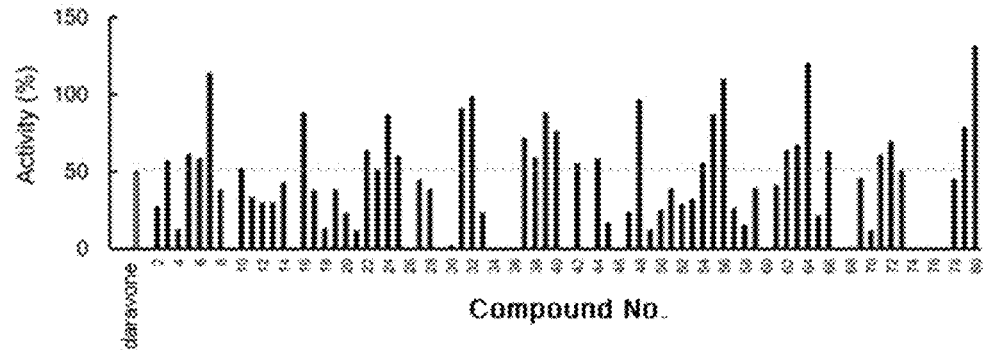
Figure 13C:
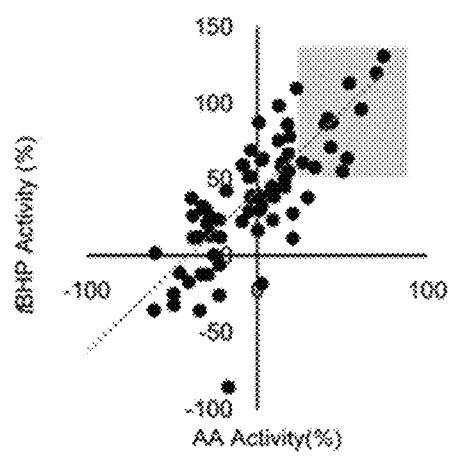
Figure 13D:
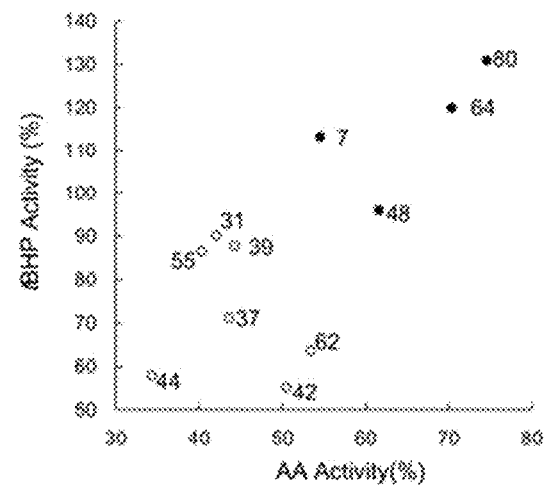

In the AA-added system, 40 compounds of the 80 compounds had activity values below 0%, that is, did not inhibit the lipid peroxidation reaction in the cultured cell system. On the other hand, 40 compounds inhibited lipid peroxidation reaction. Of these, 32 compounds showed higher activity than Edaravone (FIG. 13A). In the tBHP-added system, 17 compounds of the 80 compounds were below the activity value of 0%, while 63 compounds inhibited the lipid peroxidation reaction. Of these, 31 compounds showed higher activity than Edaravone (FIG. 13B). The activity values in the two systems were plotted (FIG. 13C), and the four compounds that showed high activity values in both systems, Compound Nos. 7, 48, 64 and 80, were decided as hit compounds (FIG. 13D), and proceed to tertiary screening.

Compound 7:
2-((4-(Phenylamino)phenyl)amino)-N-(4-sulfamoylphenyl)propanamide

Compound 48:
2,6-Dimethoxy-4-(2-(8-nitroquinolin-2-yl)vinyl)phenol

Compound 64:
$N^2,N^2$-Dimethyl-9H-fluorene-2,3-diamine

Compound 80:
N-(3-Methoxy-4-((3-methyl-1-10H-indolo[3,2-b]quinolin-11-yl)amino)phenyl)methanesulfonamide

[Formula 4]

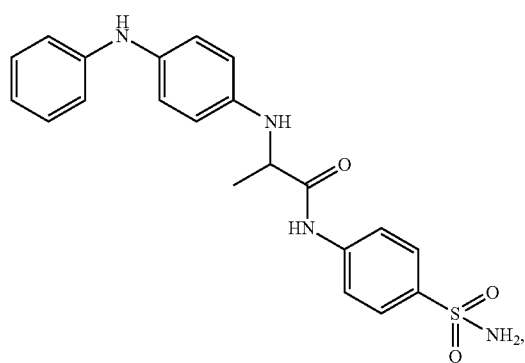

Compound 7

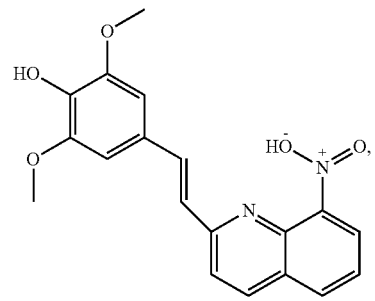

Compound 48

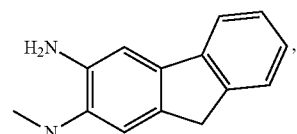

Compound 64

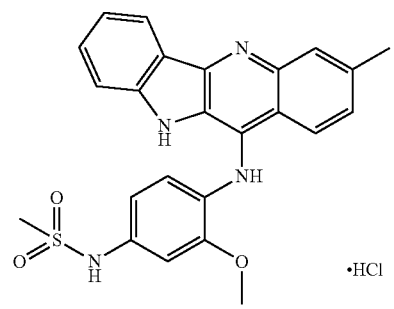

Compound 80

Example 14

Secondary Screening Using Core Library of Drug Discovery Initiative, the University of Tokyo (MTT Assay)

Secondary screening was performed for 80 compounds selected in the primary screening.

For the compounds, 10 mM 100% DMSO solutions (dispensed at 5.0 µL/well) were provided from Drug Discovery Initiative, the University of Tokyo. 495 µL of DMEM medium for measurement was added, and 1.0% DMSO solution containing 100 µM of the compound was prepared. This solution was dispensed by 80 µL with Biomek NXP into a measuring plate on which cells were seeded in advance. To the test compound (100 µM 1.0% DMSO), 64 µL of DMEM medium, 16 µL of PBS in which AA (1000 µM, 5.0% ethanol) or tBHP (1000 µM) was dissolved were manually dispensed. The final concentration was 5.0 µM NBD-TEEPO compound, 50 µM test compound, and 100 µM AA or tBHP in DMEM medium (0.5% DMSO, 0.5% acetonitrile). After 24 hours, the medium was exchanged, and MTT solution (0.5 mg/mL, 0.5% DMSO) was added. Then, cells were incubated for 24 hours, and the solution was removed. 100 µL of DMSO was added, and the absorbance at 630 nm was measured. The cell viability was calculated according to the expression described herein, with regarding the case without AA or tBHP as 100%.

The results are shown in FIGS. 14A-FIG. 14D.

Figure 14A:
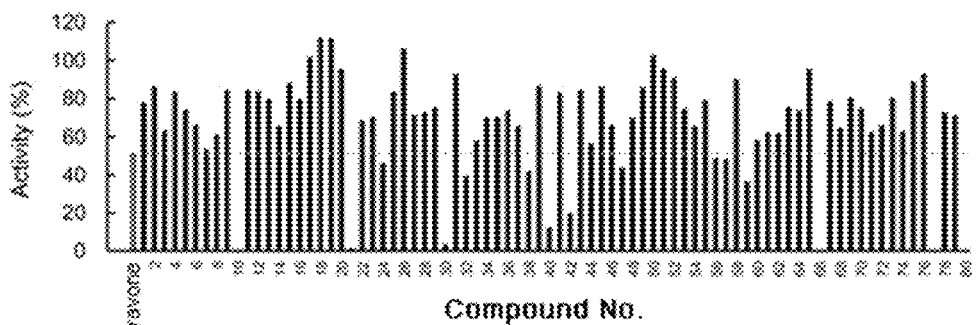
FIGS. 14A-FIG. 14D is charts showing the results of secondary screening using Core Library of Drug Discovery Initiative, the University of Tokyo, according to an MTT assay method. To 1.0×10$^4$ HepG2 cells, 100 μM AA or tBHP and 50 μM compound were added, and the cell viability after 24 hours was measured by an MTT assay. The dotted lines in FIG. 14A and FIG. 14B represent the activity value of Edaravone.
Figure 14B:
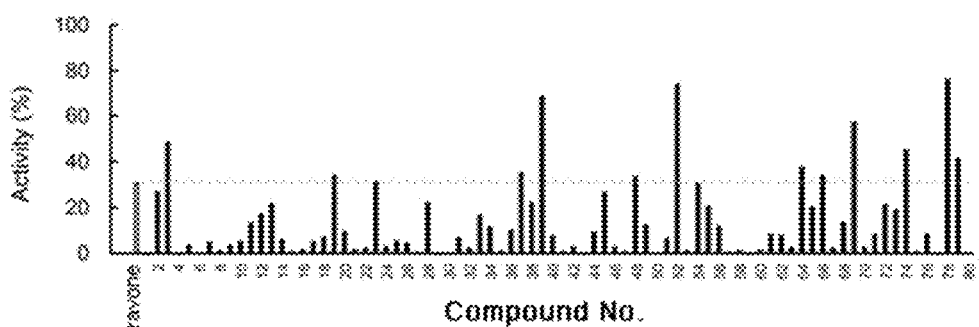
Figure 14C:
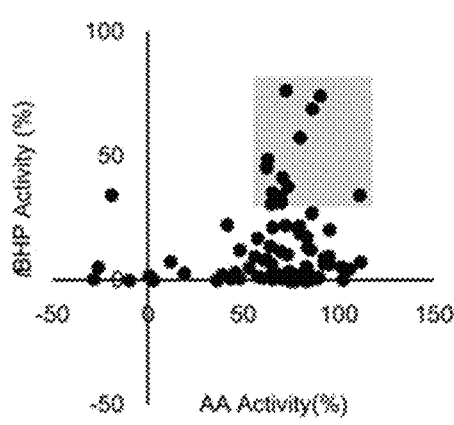
Figure 14D:
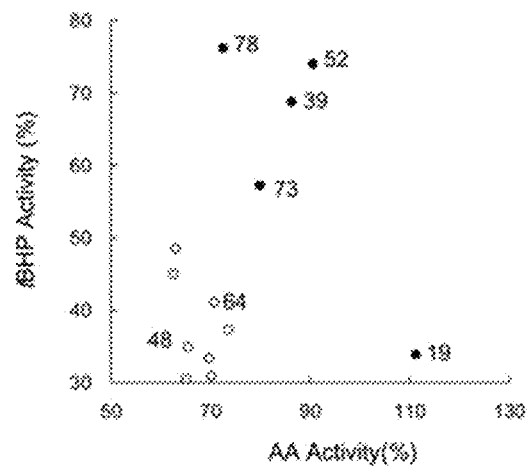

In the AA-added system, 6 compounds of the 80 compounds had activity values below 0%, that is, did not inhibit cell death caused by AA stimulation. On the other hand, 74 compounds inhibited cell death caused by AA stimulation. Of these, 64 compounds showed higher activity than Edaravone (FIG. 14A). In the tBHP-added system, 8 compounds of the 80 compounds were below the activity value of 0%, while 73 compounds inhibited cell death caused by tBHP stimulation. Of these, 14 compounds showed higher activity than Edaravone (FIG. 14B). The inhibition rates in the two systems were plotted (FIG. 14C), and five compounds which showed high inhibition rates in both systems, Compound Nos. 19, 39, 52, 73, and 78, were decided as hit compounds (FIG. 14D), and proceeded to tertiary screening.

Compound 19:
N-(2-Chlorophenyl)-5-(2-(1-pyridin-2-yl)ethylidene)hydrazinyl)-1,3,4-thiadiazol-2-amine Compound 39:
1-(7,7-Dimethyl-2-oxobicyclo[2.2.1]heptan-1-yl)-N-(1-hydroxy-2,2,6,6-tetramethylpiperidin-4-yl)-N-methylmethanesulfonamide Compound 52:
Methyl 3-amino-4-(phenylamino)benzoate Compound 73:
3-(2-(3-(2-Hydroxyethoxy)phenyl)-3-((2-morpholinoethyl)amino)imidazo[1,2-a]pyridin-6-yl)benzamide Compound 78:
1-(4-(Trifluoromethoxy)phenyl)indolin-5-amine

[Formula 5]

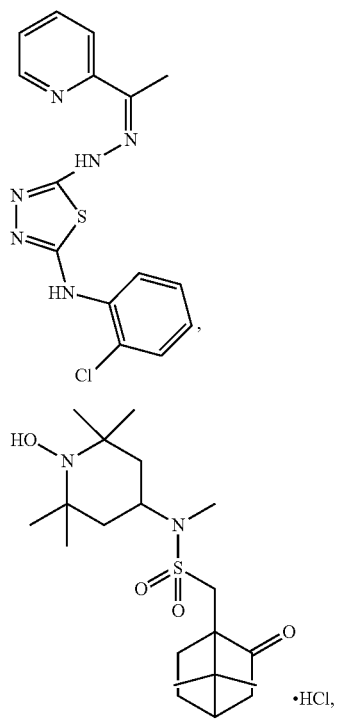

Compound 19

Compound 39

Compound 52

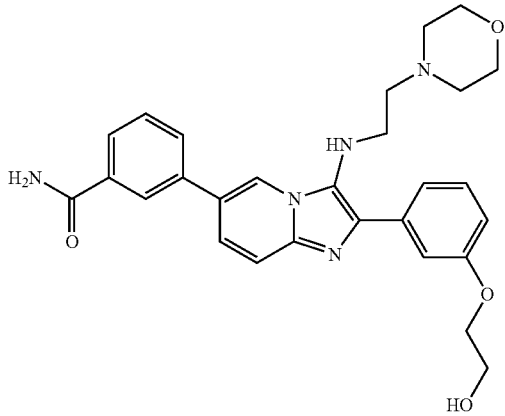

Compound 73

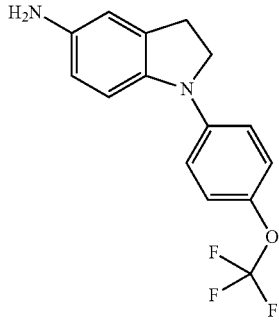

Compound 78

Example 15

Tertiary Screening Using Core Library of Drug Discovery Initiative, the University of Tokyo (NBD-TEEPO Assay)

The Core Library of Drug Discovery Initiative, the University of Tokyo, includes structural analogs for each compound. Then, secondary screening was also performed for structural analog compounds for each candidate compound in the same manner as Example 13 and the activity values were evaluated.

Specifically, the nine hit compounds, Compound Nos. 7, 19, 39, 48, 52, 64, 73, 78, 80, of the secondary screening had 5, 2, 4, 6, 6, 5, 5, 10, 2 structural analogs, respectively, thus, a total 45 structural analogs were taken. Then, including the original 9 compounds, a total 54 compounds were subjected to tertiary screening, and the activity values were calculated in the same manner.

The results are shown in FIGS. 15A-FIG. 15D, FIGS. 16A-FIG. 16D and FIG. 17.

Figure 15A:
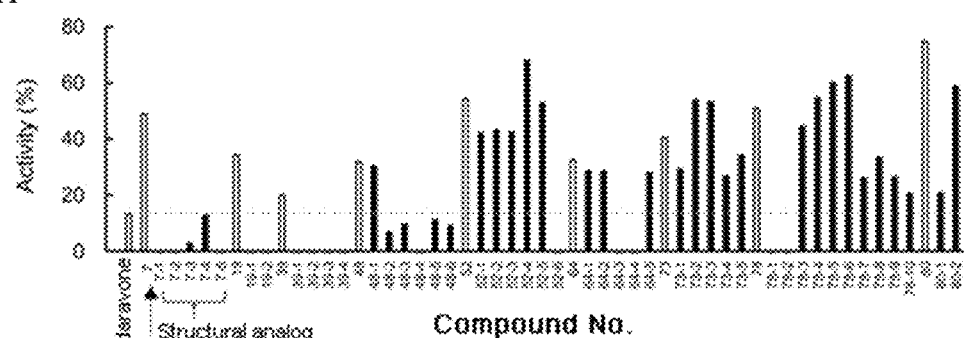
FIGS. 15A-FIG. 15D is charts showing the results of tertiary screening using Core Library of Drug Discovery Initiative, the University of Tokyo. To $1.0 \times 10^4$ HepG2 cells, 5.0 μM NBD-TEEPO, 200 μM AA or 300 μM tBHP and 50 μM compound were added, and changes of the fluorescence intensity ($\lambda_{Ex}/\lambda_{Em}$=470/530 nm) were measured (white bar: activity value of the compound of original structure, black bar: activity value of a structural analog, dotted line: activity value of Edaravone).
Figure 15B:
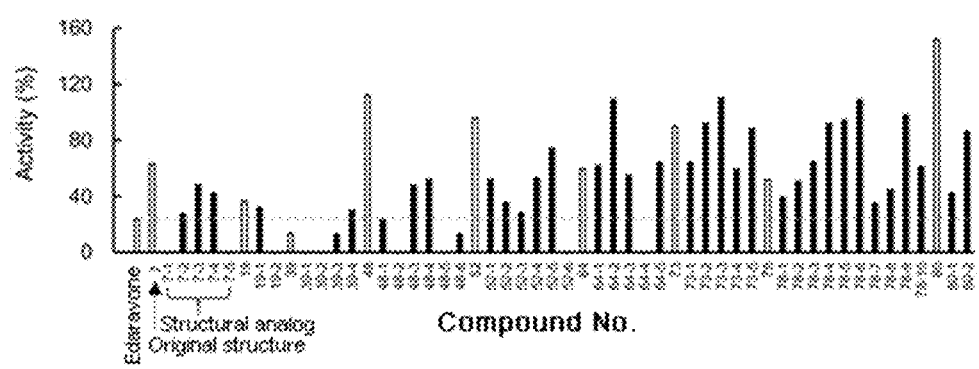

1) First, in the assay using NBD-TEEPO, when the AA-added system was used, 15 compounds out of 54 compounds had activity values below 0%, that is, did not inhibit lipid peroxidation reaction, while 39 compounds inhibited lipid peroxidation reaction. Of these, 33 compounds showed higher activity than Edaravone (FIG. 15A). When the tBHP-added system was used, 9 compounds of the 54 compounds were below the activity value of 0%, while 45 compounds inhibited lipid peroxidation reaction. Of these, 41 compounds showed higher activity than Edaravone (FIG. 15B).

Figure 16A:
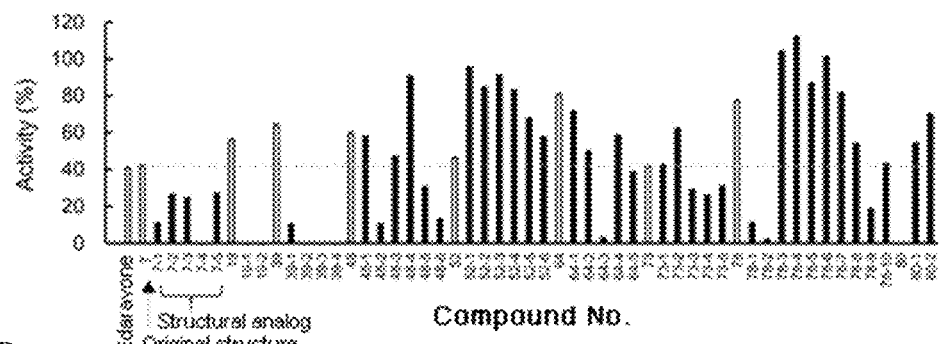
FIGS. 16A-FIG. 16D is charts showing the results of tertiary screening using Core Library of Drug Discovery Initiative, the University of Tokyo, according to an MTT assay method. To $1.0 \times 10^4$ HepG2 cells, 100 μM AA or tBHP and 50 μM compound were added, and the cell viability after 24 hours was measured by an MTT assay (white bar: activity value of the compound of original structure, black bar: activity value of a structural analog compound, dotted line: activity value of Edaravone).
Figure 16B:
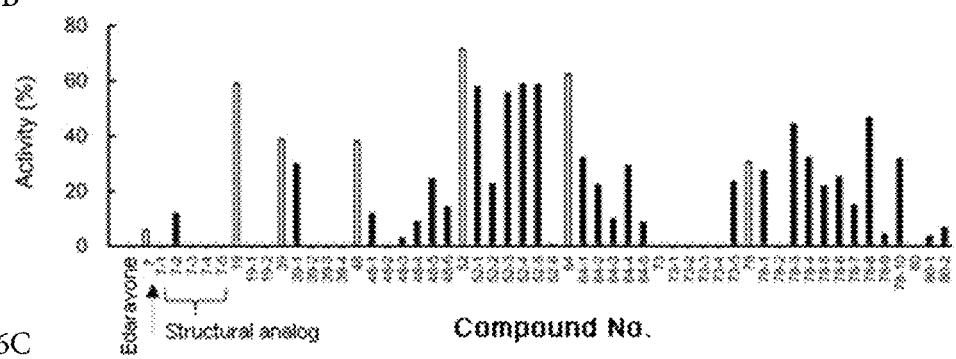
Figure 18A:
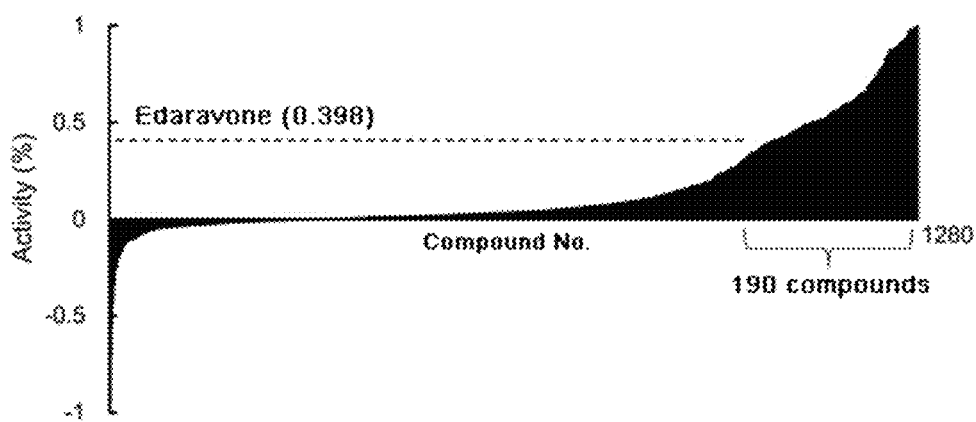
FIGS. 18A-FIG. 18B is charts showing the results of primary screening using Prestwick Chemical Library. Liposomes (2.5 mg/mL EggPC, 0.1 mg DCP), 5.0 μM NBD-TEEPO and a reaction initiator were mixed and the fluorescence intensity changes ($\lambda_{Ex}/\lambda_{Em}$=470/530 nm) were measured.
Figure 18B:
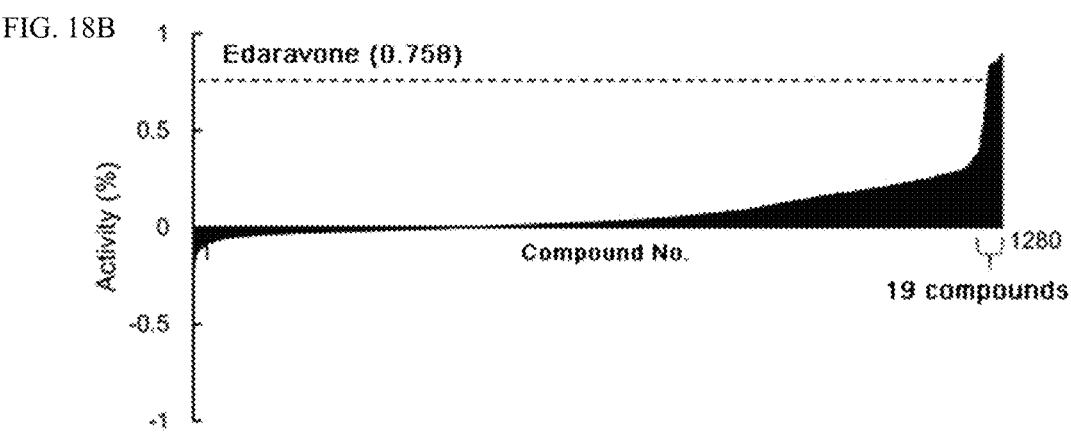

2) Then, in the MTT assay, when the AA-added system was used, 7 out of 54 compounds had activity values below 0%, that is, did not inhibit cell death caused by AA stimulation, while 47 compounds inhibited cell death caused by AA stimulation. Of these, 31 compounds showed higher activity than Edaravone (FIG. 16A). When the tBHP-added system was used, 17 compounds of the 54 compounds were below the activity value of 0%, while 37 compounds inhibited cell death caused by tBHP stimulation. Of these, 37 compounds showed higher activity than Edaravone (FIG. 18B).

3) Then, test compounds alone were further incubated for 72 hours, and evaluation of cytotoxicity thereof was performed. For the evaluation of cytotoxicity, 50 μM antioxidant was added to HepG2 cells in DMEM medium (0.5% DMSO), and after incubation at 37° C. for 72 hours, the cell viability was measured.

Figure 15C:
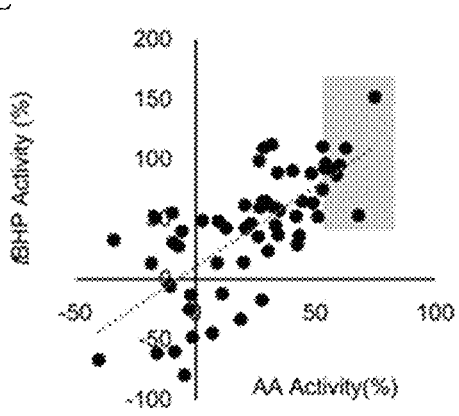
Figure 15D:
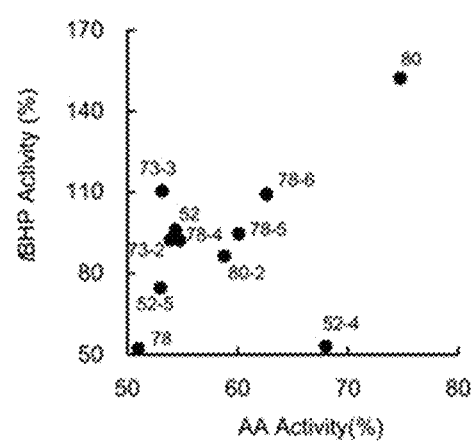
Figure 16C:
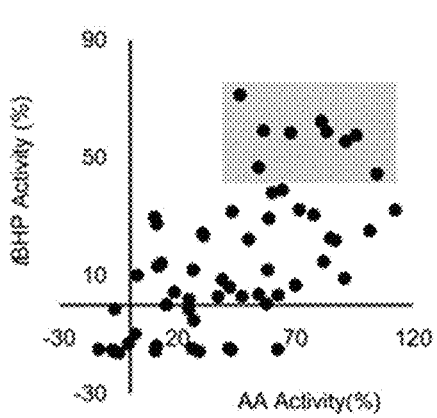
Figure 16D:
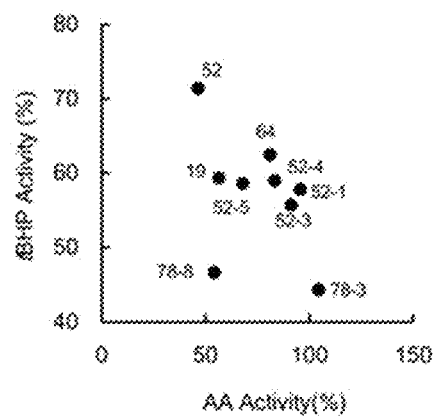

4) The activity values of the two-added systems in each of the assay using NBD-TEEPO and the MTT assay were plotted (FIG. 15C and FIG. 16C). As the result, Compound No. 52 analogs (Compound Nos. 52, 52-1, 52-3, 52-4, 52-5) and Compound No. 78 analogs (Compound Nos. 78, 78-3, 78-4, 78-5, 78-6, 78-8) showed high lipid peroxidation inhibitory effects and cell death inhibitory effects (FIG. 15D and FIG. 16D).

Figure 17:
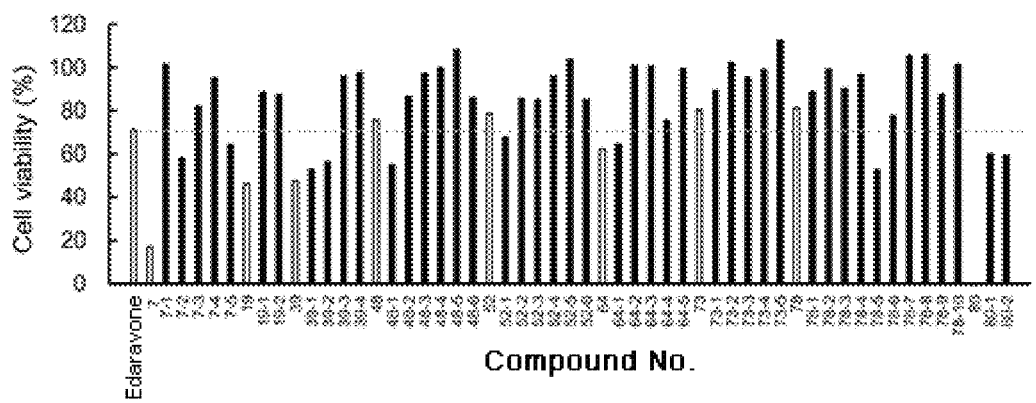
FIG. 17 is a chart showing the result of a test for cytotoxicity evaluation at tertiary screening using Core Library of Drug Discovery Initiative, the University of Tokyo. To $1.0 \times 10^4$ HepG2 cells, 50 μM compound were added, and cell viability after 72 hours was measured by an MTT assay. The dotted line represents the cell viability at 72 hours after incubation with Edaravone.

Compound No. 80 analogs (Compound Nos. 80 and 80-2) showed the highest lipid peroxidation inhibitory effect, but cytotoxicity of the compounds was extremely high (FIG. 17).

Among the compound No. 52 and its analogs (Compound Nos. 52-1 to 52-6), those that exhibited lipid peroxidation inhibitory effects have a skeleton A represented by the structure below as a common structure. The skeleton A has been reported to have antioxidant activity (Hu ML., et al., Nutr. Biochem., 1995, 6, 504-508).

Among compounds No. 78 and its analogs (Compound Nos. 78-1 to 78-10), those that exhibited lipid peroxidation inhibitory effects have a skeleton B represented by the structure below as a common structure.

[Formula 6]

Skeleton A

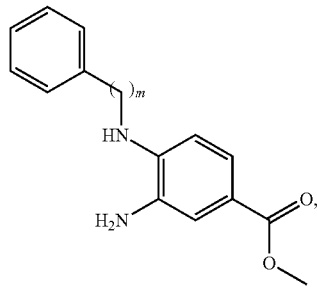

m = 0 or 1

Skeleton B

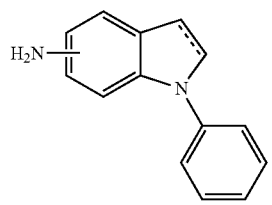

From the above results, it is suggested that compounds having the skeleton A or B, which is a common structure of compounds found as candidate compounds by the screening of the present invention, are very likely to be prominent as lipid peroxidation inhibitors.

Compound 52-1:
Methyl 3-amino-4-((4-methoxyphenyl)amino)benzoate

Compound 52-2:
Methyl 3-amino-4-((2-methoxyphenyl)amino)benzoate

Compound 52-3:
Methyl 3-amino-4-((3-methoxyphenyl)amino)benzoate

Compound 52-4:
Methyl 3-amino-4-(benzylamino)benzoate

Compound 52-5:
Methyl 3-amino-4-((1-phenylethyl)amino)benzoate

Compound 52-6:
N-(2-(phenylamino)phenyl)acetamide

[Formula 7]

Compound 52-1

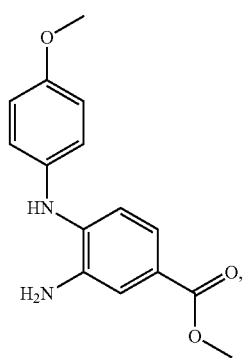

Compound 52-2

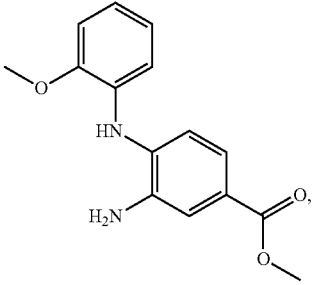

Compound 52-3

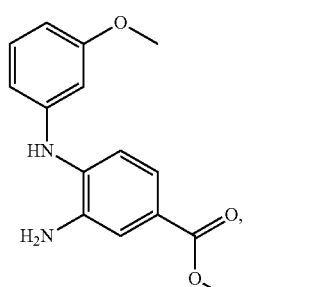

Compound 52-4

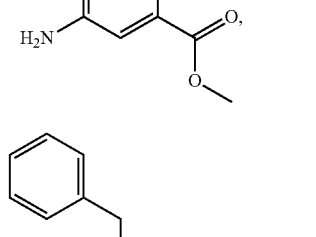

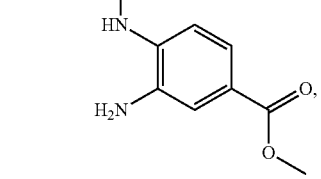

Compound 52-5

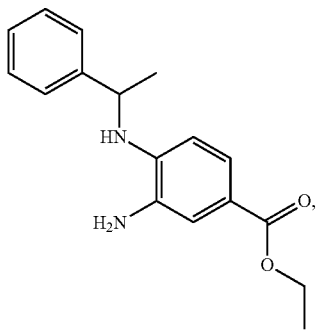

Compound 52-6

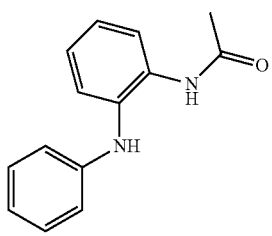

Compound 78-1:
1-(3,5-dimethylphenyl)indolin-2,3-dione
Compound 78-2:
1-(3,5-Dimethylphenyl)-3,3-difluoroindolin-2-one
Compound 78-3:
1-(3,5-Dimethylphenyl)-1H-indol-6-amine
Compound 78-4:
1-(3,5-Dimethylphenyl)indolin-6-amine
Compound 78-5:
1-(4-Methoxyphenyl)-1H-indol-5-amine
Compound 78-6:
1-(4-(Methylthio)phenyl)-1H-indol-5-amine
Compound 78-7:
1-(4-(Trifluoromethyl)phenyl)-1H-indol-5-amine
Compound 78-8:
1-(4-(Trifluoromethoxyphenyl)-1H-indol-5-amine
Compound 78-9:
1-(4-(Methylthio)phenyl)indolin-5-amine
Compound 78-10:
1-(4-(Trifluoromethyl)phenyl)indolin-5-amine

[Formula 8]

Compound 78-1

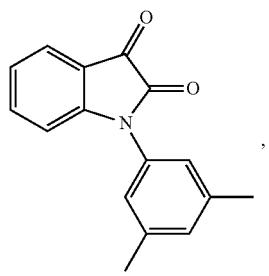

Compound 78-2

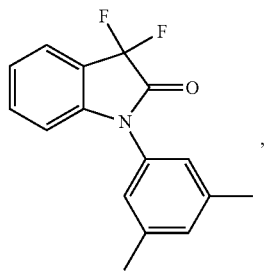

Compound 78-3

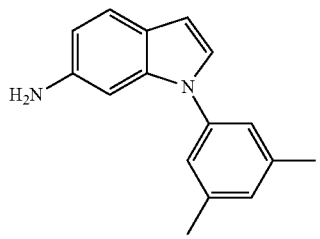

Compound 78-4

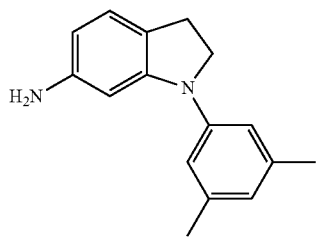

Compound 78-5

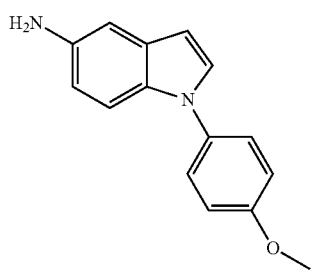

Compound 78-6

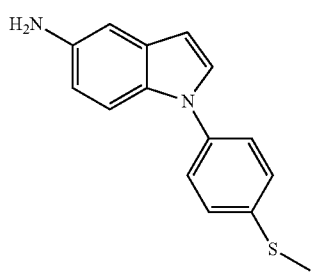

Compound 78-7

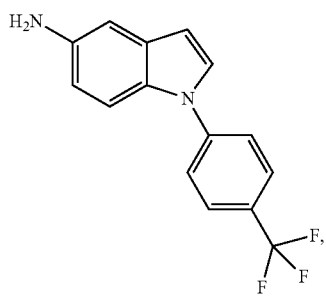

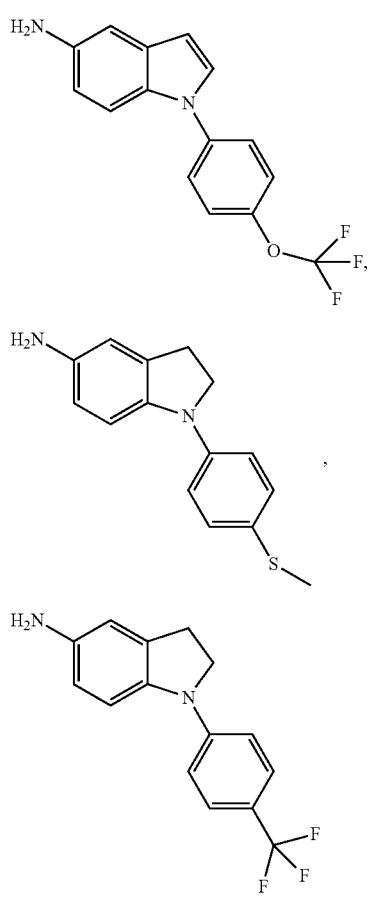

Compound 78-8

Compound 78-9

Compound 78-10

Example 16

Prestwick Chemical Library Primary Screening (AAPH System)

In the primary screening, in the AAPH and $Fe^{2+}$ systems, measurement was conducted for 1280 compounds as test compounds, respectively. The experiment method and the calculation method of the activity value were performed in the same manner as in the above case in which the Core Library of Drug Discovery Initiative, the University of Tokyo, was used. For the test compounds, solutions diluted to 20 µM (dispensed at 20 µL/well) in phosphate buffer (10 mM, pH 7.4, 2% DMSO) were provided from the Kyushu University Compound Library Drug Discovery Advanced Research and Education Platform Center.

First, when the AAPH system assay was used, Solution A containing liposomes (10 mg/mL Egg PC, 0.4 mg/mL DCP) and NBD-TEEPO compound (20 µM) in phosphate buffer (10 mM, pH 7.4, 2.0% acetonitrile) and Solution B containing AAPH 80 mM in phosphate buffer (10 mM, pH 7.4) were prepared. 10 µL each of solutions A and B were dispensed with Multidrop Combi. The final concentration was liposomes (2.5 mg/mL Egg PC, 0.1 mg/mL DCP), 5.0 µM NBD-TEEPO compound, 10 µM test compound, and 20 mM AAPH in phosphate buffer (10 mM, pH 7.4, 0.5% acetonitrile, 1% DMSO). After 40 minutes at 37° C., the fluorescence intensity at an excitation wavelength of 470 nm and a fluorescence wavelength of 530 nm was measured.

Example 17

Prestwick Chemical Library Primary Screening ($FeSO_4$ System)

Then, $Fe^{2+}$ system assay was used, and solution A containing liposomes (10 mg/mL Egg PC, 0.4 mg/mL DCP) and 20 µM of NBD-TEEPO compound in phosphate buffer (10 mM, pH 7.4, 2.0% acetonitrile) and Solution B containing 4.0 mM $FeSO_4$ in distilled water were prepared. 10 µL each of solutions A and B were dispensed with Multidrop Combi. The final concentration was liposomes (2.5 mg/mL Egg PC, 0.1 mg/mL DCP), 5.0 µM NBD-TEEPO compound, 10 µM test compound and 1.0 mM $FeSO_4$ in phosphate buffer (10 mM, pH 7.4, 0.5% acetonitrile, 1% DMSO). After 180 minutes at 37° C., the fluorescence intensity at an excitation wavelength of 470 nm and a fluorescence wavelength of 530 nm was measured.

The results are shown in FIGS. 18A-FIG. 18B and FIGS. 19A-FIG. 19C.

1) As a result, in the AAPH system, 330 compounds of the 1280 compounds had activity values below 0, that is, did not inhibit lipid peroxidation reaction, while 950 compounds inhibited lipid peroxidation reaction. Of these, 190 compounds showed higher activity values than the known compound Edaravone (FIG. 18A). In the $Fe^{2+}$ system, 434 compounds of the 1280 compounds had activity values below 0, while 846 compounds inhibited lipid peroxidation reaction. Of these, 19 compounds showed higher activity values than the known compound Edaravone (FIG. 18B).

Figure 19A:
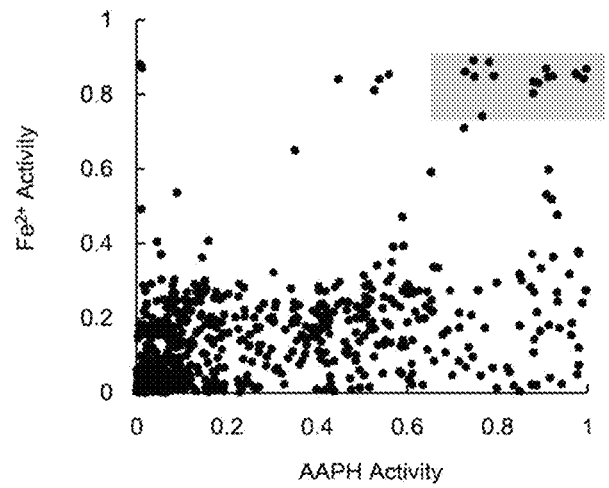
FIGS. 19A-FIG. 19C is charts showing the results of primary screening using Prestwick Chemical Library and the relationship between candidate compounds and target disease areas.
Figure 19B:
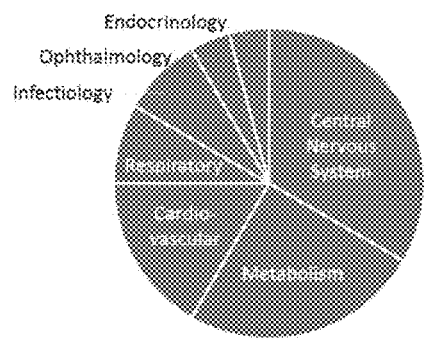
Figure 19C:
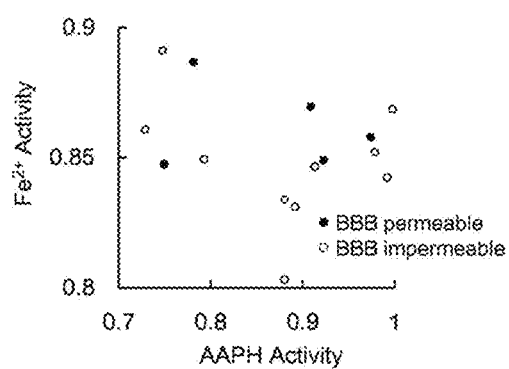

From the combined results in the AAPH and $Fe^{2+}$ systems, 16 hit compounds were obtained (FIG. 19A and FIG. 19C).

2) Since the Prestwick Chemical Library is a compound library of compounds with known pharmacological activity, information on the action point, pharmacokinetics, safety and the like can be obtained from the database and bibliographic information provided by this library. Based on these information, narrowing of the 16 hit compounds was performed. These hit compounds included therapeutic drugs of a wide range of disease areas such as the cardiovascular system, the central nervous system, the respiratory system, and antibacterial drugs (FIG. 19B).

(Pharmacological Test)

Pharmacological activity for age-related macular degeneration (AMD) was examined.

A test was performed using a light irradiation model, which is widely employed as an atrophic AMD model mouse, as a test model. Test compounds were narrowed down from the 16 candidate compounds selected by the screening for the Prestwick Chemical Library to the following 5 compounds (Compound V, Compound W, Compound X, Compound Y, Compound Z) which have been reported to be highly permeable to blood-retinal barrier (BRB), and the pharmacological activity thereof was examined.

Compound V:

Apomorphine ((R)-(−)-apomorphine hydrochloride)

This compound is known as an anti-Parkinson drug that acts on dopamine $D_1D_2$ receptors.

Compound W:

Etheroline ((−)-eseroline fumarate)

This compound is known to act on opioid receptors to have analgesic effects.

Compound X:

Ethoxyquin (6-ethoxy-2,2,4-trimethyl-1,2-dihydroquinoline)

This compound is known to have an antioxidant action.

Compound Y:

Methyldopa (Methyldopa sesquihydrate)

This compound is known as a blood pressure lowering drug that acts on adrenergic $\alpha_2$ receptors.

Compound Z:

Olanzapine (2-methyl-4-(4-methyl-1-piperazinyl)-10H-thieno[2,3-b][1,5]benzodiazepine This compound is known as an antipsychotic drug that acts on many receptors.

[Formula 9]

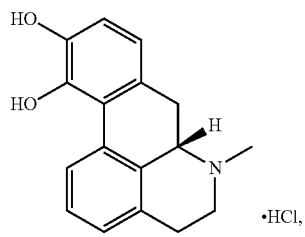

Compound V

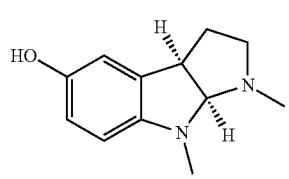

Compound W

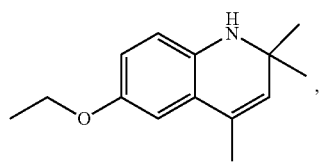

Compound X

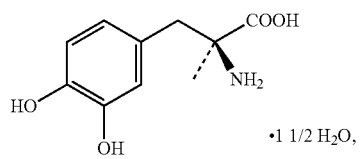

Compound Y

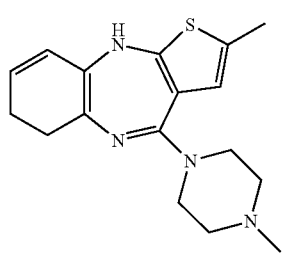

Compound Z (Procedures)

First, AMD model mice were produced according to the following schedule.

Laboratory Animals

Male BALB/c mice (4 weeks old) were purchased from Japan SLC, Inc., and allowed to acclimate for a week before being used for experiments. Laboratory animal chow (CLEA Rodent Diet CE-2, CREA JAPAN, INC.) was used as food, and tap water was freely consumed as drinking water. The animals were raised under light and dark cycles of every 12 hours. All animal experiments were conducted under the approval of the Kyushu University Animal Experiment Committee.

Production of Light-Induced AMD Model Mice

Figure 20A:
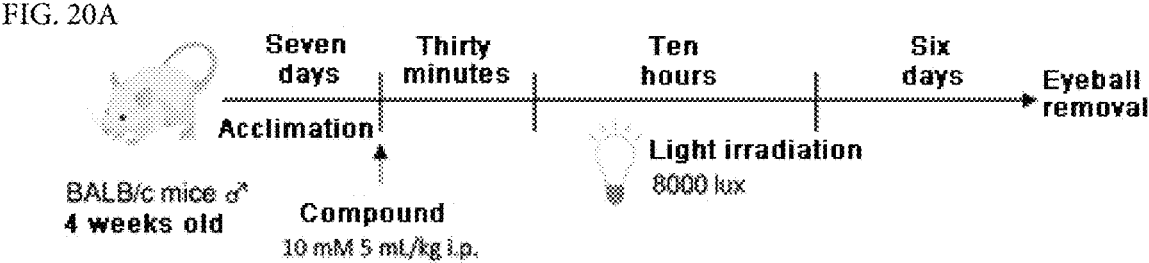
FIGS. 20A-FIG. 20B is charts showing a method for producing age-related macular degeneration (AMD) model mice.

To BALB/c mice, 5 mL/kg of 10 mM compound dissolved in PBS containing 10% polyethylene glycol (PEG) 300 was intraperitoneally administered. Thirty (30) minutes later, a drop of Midrin P (5 mg/mL tropicamide, 5 mg/mL phenylephrine hydrochloride; Santen Pharmaceutical Co., Ltd.) was applied to each eye as a mydriatic. The mice were irradiated with 8000 lux white light for 10 hours, then returned to under normal light and dark cycles, and raised for 6 days. On day 7, the animal was euthanized by cervical dislocation, and the eyeballs were removed (FIG. 20A).

Figure 20B:
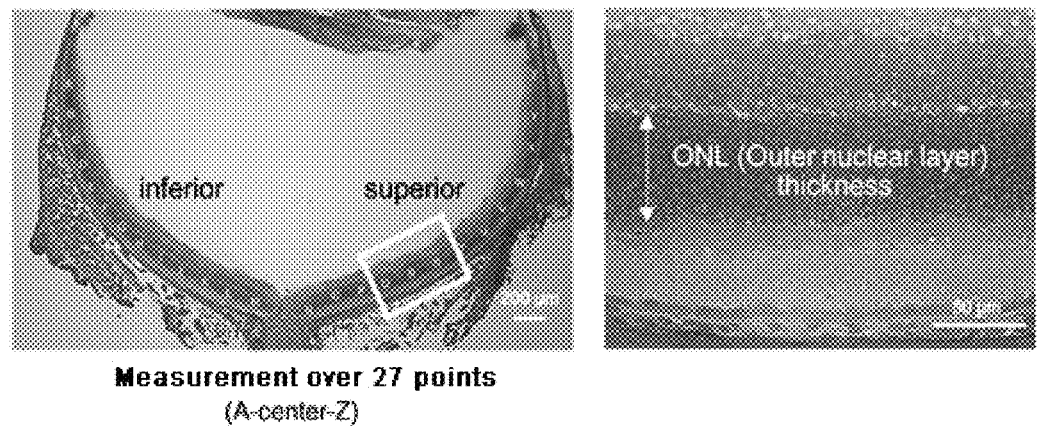

Preparation of Frozen Eyeball Section 10 mM of the test compound was dissolved in PBS containing 10% PEG 300, and the obtained solution was administered once to male BALB/c mice intraperitoneally at a dose of 5 mL/kg. From thirty minutes after the administration, the mice were irradiated with 8000 lux white light for 10 hours. Then, they were raised under normal light and dark cycles for 6 days. On day 7, the animals were euthanized, then the eyeballs were removed. Frozen sections of 8 μm thickness were prepared and subjected to hematoxylin eosin (HE) staining, and the thickness of the outer nuclear layer (ONL) was measured over 27 points every 180 μm (FIG. 20B).

HE Staining

The preparation was air-dried for 1 hour, fixed with acetone at room temperature for 15 minutes, then immersed in 99.5% EtOH, 80% EtOH, 70% EtOH, and purified water in this order for 3 minutes each, and stained with hematoxylin for 10 minutes. Then, it was washed with running water for 10 minutes, soaked in warm water for 1 minute, and stained with eosin for 1.5 minutes. After washing with purified water, it was immersed in 70% EtOH, 80% EtOH, and 99.5% EtOH in this order for 3 minutes each, then washed with xylene three times, dried, and then enclosed with VectaMount™ Mounting Medium. The resultant was subjected to observation and imaging with Keyence fluorescence microscope (BZ-9000).

Statistical Analysis

Results were expressed as mean+standard deviation. Dunnett's Test was used for multigroup comparison.

(Results)

Figure 21A:
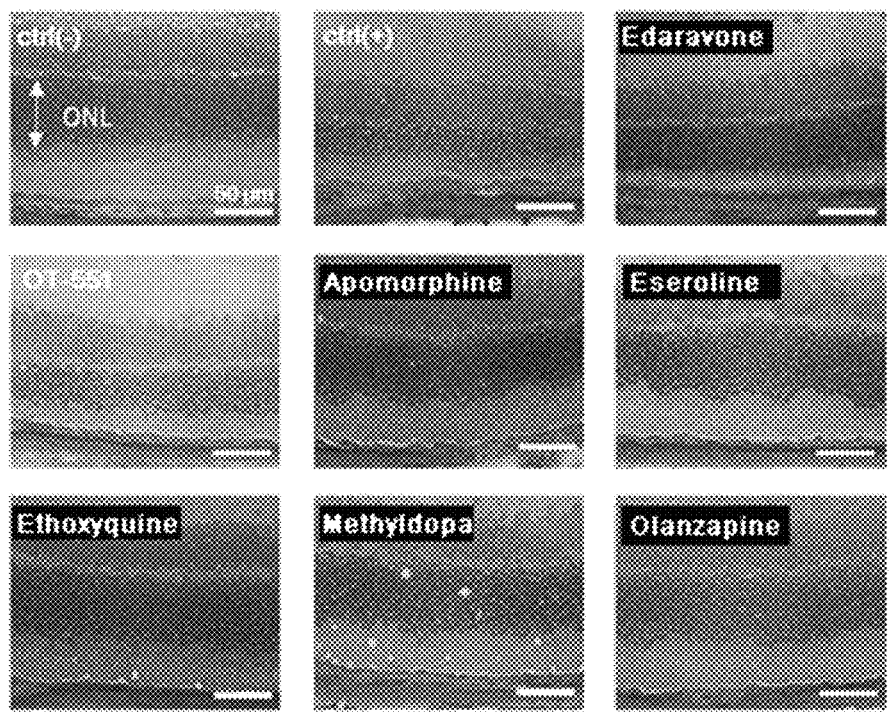
FIGS. 21A-FIG. 21C is charts showing the results of evaluating the thickness of an outer nuclear layer (ONL).
Figure 21B:
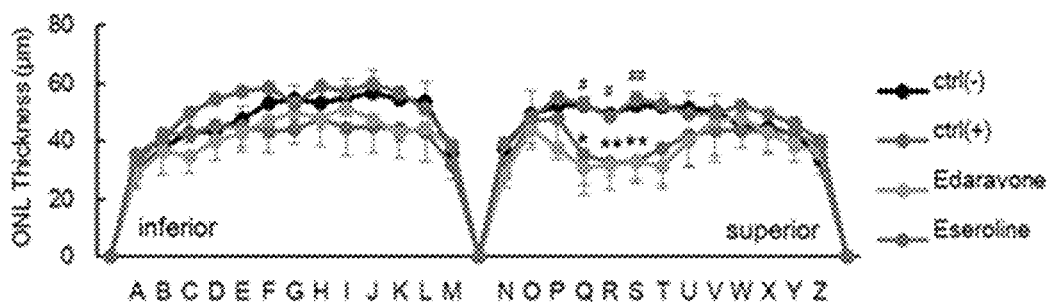
Figure 21C:
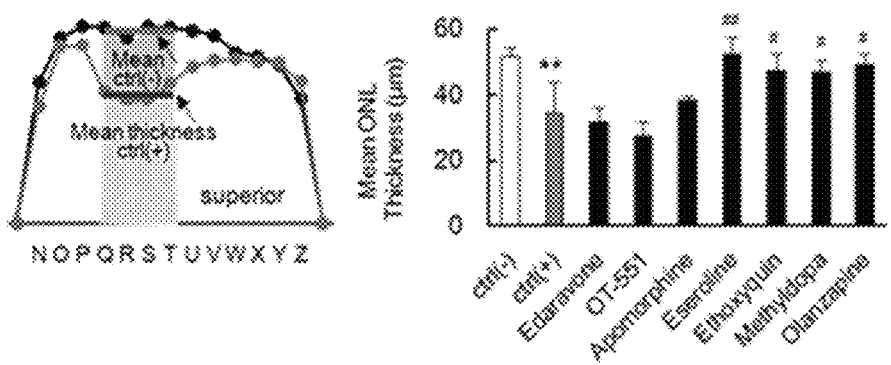

The imaging results are shown in FIGS. 21A-FIG. 21C. The figures include an inner nuclear layer (INL) in the top, an outer nuclear layer (ONL) in the middle, and a retinal pigment epithelium (RPE) in the bottom. When cell death occurs due to lipid peroxidation, the thickness of the outer nuclear layer in the middle becomes thinner.

First, the thickness of ONL was significantly reduced by light irradiation (see, FIG. 21A negative control). The extent of ONL disorders was particularly severe on the superior side of the eyeball (FIG. 21B), and these results were consistent with the results known from the literature (see, for example, Tanito M., et al., Invest. Ophthalmol. Vis. SCI., 2007, 48 (4), 1900-5.).

On the other hand, in the case of the five test compounds used in this study, the ONL thickness in either case did not differ so much compared to that of the positive control, and significant thicknesses were observed compared to that of Edaravone and OT-551 as control compounds even at the same dose of 50 μmol/kg (FIG. 21C).

For OT-551, which is a compound known to have a high retinal protective effect, approximately 100 mg/kg (360 μmol/kg) has been reported to be required in a light irradiation model mouse. Thus, the dose 50 μmol/kg in this study, about one-seventh of that of OT-551, is a considerably low dose.

In addition, 50 μmol/kg is less than one-tenth of each median lethal dose (LD50) of the five test compounds, thus the compounds have been confirmed to be safe (see FIG. 22).

From the above results, it was suggested that the compounds selected by the screening of the present invention are useful compounds for age-related macular degeneration.

INDUSTRIAL APPLICABILITY

According to the assay method, the assay kit, and the screening reaction using the fluorophore compound of the present invention, it is easy to explore a compound having lipid peroxidation inhibitory activity. Furthermore, candidate compounds according to the screening methods of the present invention are useful for treating lipid peroxidation reaction-induced diseases, such as age-related eye diseases.

The invention claimed is:
1. An assay kit for detecting lipid peroxidation inhibitory activity of a test compound, comprising:
a compound represented by formula (I):

[Formula 1]

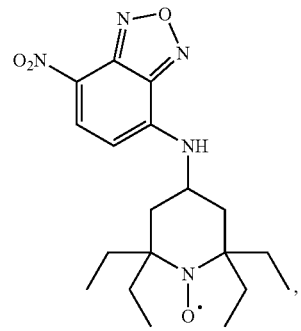

(I)

a liposome, and
at least one compound selected from the group consisting of 2,2'-azobis(2-aminopropane) dihydrochloride and a divalent iron ion source material
in a buffer.
2. The assay kit according to claim 1, wherein the divalent iron ion source material is iron(II) sulfate.
3. The assay kit according to claim 1, comprising a package insert showing an activity value of a compound having lipid peroxidation inhibitory activity.
4. An assay kit comprising any two or more of the assay kits according to claim 1.

* * * * *